(12) United States Patent
Hammadi et al.

(10) Patent No.: US 11,918,675 B2
(45) Date of Patent: Mar. 5, 2024

(54) ORAL CARE COMPOSITIONS

(71) Applicant: Colgate-Palmolive Company, New York, NY (US)

(72) Inventors: Salima Hammadi, Somerville, NJ (US); Harsh Mahendra Trivedi, Hillsborough, NJ (US); Melissa Martinetti, Bridgewater, NJ (US); David Suriano, Edison, NJ (US); Michael Fitzgerald, Oakhurst, NJ (US); Yun Xu, Langhorne, PA (US); Shashank Potnis, Thane (IN); Karthik Sambanthamoorthy, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/247,099

(22) Filed: Nov. 30, 2020

(65) Prior Publication Data

US 2021/0177724 A1 Jun. 17, 2021

Related U.S. Application Data

(60) Provisional application No. 62/948,628, filed on Dec. 16, 2019.

(51) Int. Cl.
*A61K 8/73* (2006.01)
*A61K 8/21* (2006.01)
*A61K 8/27* (2006.01)
*A61K 8/34* (2006.01)

(52) U.S. Cl.
CPC .................. *A61K 8/73* (2013.01); *A61K 8/21* (2013.01); *A61K 8/27* (2013.01); *A61K 8/345* (2013.01); *A61K 2800/48* (2013.01)

(58) Field of Classification Search
CPC .............. A61K 2300/00; A61K 31/166; A61K 31/351; A61K 31/381; A61K 31/40; A61K 31/404; A61K 31/407; A61K 31/444; A61K 31/4709; A61K 31/54; A61K 31/661; A61K 31/675; A61K 31/7076; A61K 38/06; A61K 38/063; A61K 45/06; A61K 9/0014; A61K 9/0019; A61K 9/0095; A61K 9/4866; A61K 2800/48; A61K 8/21; A61K 8/27; A61K 8/345; A61K 8/73; A61Q 11/00; C07K 5/0819; C07H 19/16; C07H 19/207; A61P 39/04; A61P 39/06
See application file for complete search history.

(56) References Cited

U.S. PATENT DOCUMENTS

| | | | |
|---|---|---|---|
| 4,193,987 A | 3/1980 | Becker et al. | |
| 4,209,504 A | 6/1980 | Becker et al. | |
| 4,469,673 A | 9/1984 | Iioka et al. | |
| 5,342,631 A | 8/1994 | Yatka et al. | |
| 6,106,828 A | 8/2000 | Bisgard-Frantzen et al. | |
| 6,280,769 B1 | 8/2001 | D'Amelia et al. | |
| 7,094,759 B2 | 8/2006 | Senpuku et al. | |
| 7,226,590 B2 | 6/2007 | Chilcott et al. | |
| 8,460,643 B2 | 6/2013 | Vladimirovich et al. | |
| 8,691,190 B2 | 4/2014 | Haught et al. | |
| 8,980,230 B2 | 3/2015 | LeBlanc et al. | |
| 9,084,902 B2 | 7/2015 | Mordas et al. | |
| 9,387,969 B2 | 7/2016 | Schapiro et al. | |
| 10,034,820 B2 | 7/2018 | Farnum | |
| 10,111,840 B2 | 10/2018 | Guy et al. | |
| 2005/0048007 A1 | 3/2005 | Ruggles | |
| 2007/0098650 A1 | 5/2007 | Miller et al. | |
| 2009/0175997 A1 | 7/2009 | Ratnam et al. | |
| 2013/0029294 A1* | 1/2013 | Schapiro .............. | A61K 8/9717 433/216 |
| 2013/0344217 A1 | 12/2013 | Zhang et al. | |
| 2016/0317404 A1 | 11/2016 | Reynolds | |
| 2016/0354417 A1 | 12/2016 | Smittle et al. | |
| 2017/0216155 A1 | 8/2017 | Maloney | |
| 2018/0020707 A1 | 1/2018 | Toksoz et al. | |
| 2018/0049457 A1 | 2/2018 | Cheng et al. | |
| 2018/0282358 A1 | 10/2018 | Cheng et al. | |
| 2018/0303781 A1 | 10/2018 | Han | |
| 2018/0344585 A1 | 12/2018 | Constantine et al. | |
| 2021/0177724 A1 | 6/2021 | Hammadi et al. | |

FOREIGN PATENT DOCUMENTS

| | | |
|---|---|---|
| DE | 202009013065 U1 | 1/2010 |
| EP | 1483366 | 12/2004 |
| EP | 2486806 | 8/2012 |
| EP | 2817002 | 12/2014 |
| FR | 2953688 * | 6/2011 |
| WO | 2008/013740 | 1/2008 |
| WO | 2012/150607 | 11/2012 |
| WO | 2014/055975 | 4/2014 |
| WO | 2014/121301 | 8/2014 |
| WO | 2016/166515 | 10/2016 |
| WO | 2018/106983 | 6/2018 |
| WO | 2022/245567 | 11/2022 |

OTHER PUBLICATIONS

Doran et al., 2007, "A clinical study on the effect of the prebiotic inulin in the control of oral malodour," Microbial Ecology in Health and Disease 19(3):158-163.
Anonymous, 2019, "Specialist Toothpaste", Mintel Database GNPD AN: 6746809.
International Search Report and the Written Opinion of the International Searching Authority issued in International Application PCT/US2020/070830 dated Apr. 1, 2021.
Al'yans Krasy, 2020, "Charcoal Whitening Mouthwash", Mintel Database GNPD AN: 8253819.
Comptoirdes Lys, 2019, "Vegetable Charcoal Toothpaste with Mint and Lemon Flavour", Mintel Database GNPD AN: 6952995.
International Search Report and the Written Opinion of the International Searching Authority issued in International Application PCT/US2022/050678 dated Apr. 6, 2023.
Tom's of Maine, 2020, "Spearmint Natural Prebiotic Flouride Toothpaste", Mintel Database GNPD AN: 7501575.

\* cited by examiner

*Primary Examiner* — Lezah Roberts

(57) ABSTRACT

Described herein are oral care compositions comprising—in relevant part—an effective amount of inulin. Methods of making and using these compositions are also described.

7 Claims, No Drawings

ORAL CARE COMPOSITIONS

CROSS-REFERENCE TO RELATED PATENT APPLICATION

This application claims the benefit of priority from U.S. Provisional Patent Application No. 62/948,628, filed Dec. 16, 2019, the contents of which are hereby incorporated herein in their entirety.

BACKGROUND

Although oral malodor or bad breath is an unpleasant condition experienced by most individuals, it typically results in transient discomfort. At least 50 percent of the population suffer from chronic oral malodor, however, and approximately half of these individuals experience a severe problem that creates personal discomfort and social embarrassment. The mouth air of chronic malodor sufferers is tainted with compounds such as hydrogen sulfide, methyl mercaptan, and organic acids, which produce a stream of foul air that is gravely offensive to the people in their vicinity. Sufferers often make desperate attempts to mask their oral malodor with mints and chewing gum, compulsive brushing, and repeatedly rinsing with commercial mouthwashes. While dental diseases have been strongly associated with this condition, there is considerable evidence that dentally healthy individuals can exhibit significant levels of mouth odor. Proteolytic activity by microorganisms residing on the tongue and teeth results in foul-smelling compounds, and is the most common cause of oral malodor. Interest in oral malodor research and clinical treatment has increased in the last few years, but a method of effective treatment has been elusive.

Although many advances in the art of formulating oral care composition have been made with respect to improving its ability to treat oral malodor, many more challenges remain.

BRIEF SUMMARY

The present invention is directed to an oral care composition that mitigates malodor comprising inulin. Inulin is a naturally occurring polysaccharide produced by many types of plants. Inulin is a heterogeneous collection of fructose polymers. The degree of polymerization of inulin ranges from 2 to about 60. Inulin's prebiotic mechanism of selectively promoting the growth of beneficial bacteria promotes gastrointestinal health. Further, in vivo effect of the prebiotic inulin controls oral malodor.

Inulin is present in the malodor-mitigating oral care composition in an amount that is efficacious to mitigate oral malodor. It has been found that the growth of beneficial oral health-associated bacteria significantly increased in the presence of inulin at all tested concentrations relative to untreated (0% inulin), indicating inulin fermentation. It has also been determined that the growth of tested oral malodor-associated bacteria in the presence of inulin was parity to untreated at all tested concentrations, indicating lack of inulin fermentation.

Examples of beneficial oral health-associated bacteria include *Streptococcus salivarius, Streptococcus oralis*, and *Streptococcus sanguinis*, whereas examples of oral malodor-associated bacteria include *F. nucleatum, V. parvula*.

The malodor-mitigating oral care composition comprises about 0.01 wt % to about 2 wt % of inulin, or any sub-range thereof.

Alternatively, the malodor-mitigating oral care composition comprises higher formulation dose of inulin to accommodate product dilution during use. The malodor-mitigating oral care composition comprises about 1 wt % to about 5 wt % of inulin, or any sub-range thereof.

The present invention is also directed to a malodor-mitigating oral care composition comprising inulin and further comprising a zinc ion source. A zinc ion source is a chemical compound, a complex, or a salt that supplies the oral care composition with zinc cations. Zinc ions may be furnished by any physiologically acceptable zinc salt having a measurable solubility in water. The effective portion of the zinc salts are the zinc ions, i.e., zinc cations.

Examples of zinc ion sources include zinc oxide, zinc sulfate, zinc chloride, zinc citrate, zinc lactate, zinc gluconate, zinc malate, zinc tartrate, zinc carbonate, zinc phosphate, and mixtures thereof. The zinc ion source may further be a hydrate.

The present invention is also directed to an malodor-mitigating oral care composition comprising inulin, a zinc ion source, and a humectant.

The humectant of the present invention is a hygroscopic substance used to keep the oral care composition moist. Under one embodiment, it is often a molecule with several hydrophilic groups, such as hydroxyl, amine and carboxyl groups. The carboxylic groups may be esterified. Examples of humectants includes edible polyhydric alcohols such as glycerin, sorbitol, xylitol, butylene glycol, propylene glycol, and combinations thereof. Under one embodiment, the humectant is a polyol. Such a polyol may be selected from sorbitol, glycerin, and combinations thereof. In yet another embodiment, the humectant is xylitol.

More specifically, the present invention is also directed to an malodor-mitigating oral care composition comprising inulin, a zinc ion source, and a humectant selected from the group consisting of glycerin, sorbitol, xylitol, butylene glycol, polyethylene glycol, propylene glycol, trimethyl glycine, and mixtures thereof.

Under one embodiment, the malodor-mitigating oral care composition comprises inulin, humectant and zinc ion source, wherein the weight ratio of inulin:humectant:zinc ion from zinc ion source is 5 to 50:5 to 50:1 to 10, or any sub-ranges thereof.

The present invention is also directed to an oral care product comprising the oral care composition. The oral care product means the final form which is sold or administered to the patient. The oral care product is a product that comprises mixture of chemical compounds or of chemical compositions that are applied to the oral cavity to improve the health of the patient's mouth.

The oral care product may be identical to the oral care composition, or it may comprise the oral care composition and other ingredients. Further, the form of the oral care composition or oral care product is an ingestible or non-ingestible solid, powder, liquid, a fluid, a gel, or a paste. Examples of oral care products include toothpaste, oral rinse, mouthrinse, denture cleaner, and saliva substitute.

The present invention is also directed to a toothpaste comprising the oral care composition. The oral care product comprises toothpaste ingredients usually found in toothpastes. Examples of such ingredients include a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a fluoride source, a viscosity modifier, and a mixture thereof.

The oral care composition of the present invention is designed to mitigate oral malodor. The oral malodor refers to the odor originated by gram-negative, anaerobic bacteria, or to the unpleasant smell of breath mainly originated from volatile sulfide compounds, including hydrogen sulfide, methylmercaptan, and dimethylsulfide resulting from the proteolytic degradation of peptides present in saliva, shed epithelium, food debris and gingival crevicular fluid.

The present invention is also directed to a method of mitigating oral malodor of a patient's oral cavity by applying the oral care product to a portion of the patient's oral cavity.

The invention is defined by at least twelve aspects.

In the first aspect, the invention relates to an malodor-mitigating oral care composition comprising inulin.

In the second aspect, the invention relates to an malodor-mitigating oral care composition comprising inulin, wherein the composition comprises about 0.01 wt % to about 2 wt % of inulin.

In the third aspect, the invention relates to an malodor-mitigating oral care composition comprising inulin, wherein the composition comprises about 1 wt % to about 5 wt % of inulin.

In the fourth aspect, the invention relates to an malodor-mitigating oral care composition comprising inulin, and a zinc ion source.

In the fifth aspect, the invention relates to an malodor-mitigating oral care composition comprising inulin, and a zinc ion source, wherein the zinc ion source is selected from the group consisting of zinc oxide, zinc sulfate, zinc chloride, zinc citrate, zinc lactate, zinc gluconate, zinc malate, zinc tartrate, zinc carbonate, zinc phosphate, and mixtures thereof.

In the sixth aspect, the invention relates to an malodor-mitigating oral care composition comprising inulin and a humectant selected from the group consisting of glycerin, sorbitol, xylitol, butylene glycol, polyethylene glycol, propylene glycol, trimethyl glycine, and mixtures thereof.

In the seventh aspect, the invention relates to an malodor-mitigating oral care composition comprising inulin and a humectant that is xylol.

In the eighth aspect, the invention relates to an malodor-mitigating oral care composition comprising inulin, a zinc ion source, a humectant selected from the group consisting of glycerin, sorbitol, xylitol, butylene glycol, polyethylene glycol, propylene glycol, trimethyl glycine, and mixtures thereof, wherein the weight ratio of inulin:humectant:zinc ion from zinc ion source is 5 to 50:5 to 50:1 to 10.

In the ninth aspect, the invention relates to an malodor-mitigating oral care composition comprising inulin, a zinc ion source, a humectant selected from the group consisting of glycerin, sorbitol, xylitol, butylene glycol, polyethylene glycol, propylene glycol, trimethyl glycine, and mixtures thereof, wherein the weight ratio of inulin:humectant:zinc ion from zinc ion source is 10 to 20:10 to 20:2 to 4.

In the tenth aspect, the invention relates to an malodor-mitigating oral care composition comprising inulin, wherein the oral care composition further comprises a toothpaste ingredient selected from: a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a humectant, a fluoride source, a viscosity modifier, and a mixture thereof.

In the eleventh aspect, the invention relates to an oral care product comprising the oral care composition comprising inulin, wherein the oral care product is selected from: an ingestible or non-ingestible solid, powder or liquid; a toothpaste, a mouthwash, and a mouthrinse.

In the twelfth aspect, the invention relates to a method of mitigating oral malodor of a patient's oral cavity by applying an oral care product comprising an oral care composition comprising inulin, wherein the oral care product is in a form selected from: an ingestible or non-ingestible solid, powder, or liquid; a toothpaste; a mouthwash; and a mouthrinse, to a surface of the patient's oral cavity.

DETAILED DESCRIPTION

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation.

As used herein and in the appended claims, the singular forms "a", "an", and "the" include plural references unless the context dictates otherwise. The singular form of any class of the ingredients refers not only to one chemical species within that class, but also to a mixture of those chemical species; for example, the term "surfactant" in the singular form, may refer to a mixture of compounds each of which is also considered a surfactant. The terms "a" (or "an"), "one or more" and "at least one" may be used interchangeably herein. The terms "comprising", "including", and "having" may be used interchangeably. The term "include" should be interpreted as "include, but are not limited to". The term "including" should be interpreted as "including, but are not limited to".

The abbreviations and symbols as used herein, unless indicated otherwise, take their ordinary meaning.

The abbreviation "wt %" means percent by weight.

The symbols "$\lambda$", "nm", "n". "µL", "mL", "g", and "° C." refer to wavelength, nanometer, and sample size, microliter or $10^{-6}$ liters, milliliter or $10^{-3}$ liters; gram; and a degree of Celcius. The symbol "°" refers to a degree, including a degree of an angle and a degree of Celsius. The symbol "pH" is the negative of the base 10 logarithm of the activity of the hydrogen ion.

When referring to chemical structures, and names, the symbols "C", "H", "Cl", "K", "Na", "O", "S", and "Zn" mean carbon, hydrogen, chlorine, potassium, sodium, oxygen, sulfur, and zinc, respectively.

The abbreviations "SIFT-MS", "OD610", "ANOVA", and "ppm" mean Selected Ion Flow Tube Mass Spectrometry, optical density at $\lambda=610$ nm, analysis of variance, and parts per million, respectively.

"S." in "S. salivarius", "S. oxalis", and "S. sanguinis" means Streptococcus. "F." in "F. nucleatum" means Fusobacterium. "V." in "V. parvula" means Veillonella.

The term "patient" means the person whose mouth the malodor-mitigating oral care composition or the oral care product comprising such composition is applied to. Under one embodiment, the patient is the end-user. The definition of the term "patient" also includes a person who wishes to mitigate oral malodor but is otherwise healthy. Further, the definition also includes a person who uses the oral care composition or the oral care product comprising such composition without knowing the malodor-mitigating properties of the oral care composition or the oral care product comprising such composition.

The term "about" when referring to a number means any number within a range of 10% of the number. For example, the phrase "about 5 wt %" refers to a number between, and including, 4.5000 wt % and 5.5000 wt %.

As used throughout, ranges are used as shorthand for describing each and every value that is within the range. Any value within the range can be selected as the terminus of the range.

The term "mixture" is to be interpreted broadly. It refers to a mixture of ingredients. The mixture may be a solid, liquid, semisolid. If a mixture is a liquid, a mixture may be a solution, an emulsion, a dispersion, a mixture displaying the Tyndall effect, or any other homogeneous mixture. Under one embodiment, the mixture is shelf stable. When referring to a list of ingredients, unless specifically indicated otherwise, the term "mixture" refers to a mixture of the aforementioned ingredients with each other, a mixture of any of aforementioned ingredients with other ingredients that are not aforementioned, and to a mixture of several aforementioned ingredients with other ingredients that are not aforementioned.

Any member in a list of species that are used to exemplify or define a genus may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

All references cited herein are hereby incorporated by reference in their entireties. In the event of a conflict in a definition in the present disclosure and that of a cited reference, the present disclosure controls.

The present invention is directed to an oral care composition that mitigates malodor comprising inulin.

The phrase "malodor-mitigating oral care composition" means an oral care composition for mitigating oral malodor.

Inulin is a naturally occurring polysaccharide produced by many types of plants. Inulin is a heterogeneous collection of fructose polymers. It consists of chain-terminating glucosyl moieties and a repetitive fructosyl moiety, which are linked by β(2,1) bonds. The degree of polymerization of inulin ranges from 2 to about 60.

Inulin's prebiotic mechanism of selectively promoting the growth of beneficial bacteria promotes gastrointestinal health. Further, in vivo effect of the prebiotic inulin controls oral malodor.

Under one embodiment, inulin is extracted from chicory. Alternatively, inulin may be extracted from Agave, *Agave* spp., banana, plantain, Musaceae, burdock, *Arctium lappa*, camas *Camassia* spp., *Cichorium intybus*, coneflower, *Echinacea* spp., costus, *Saussurea lappa*, dandelion, *Taraxacum officinale*, elecampane, *Inula helenium*, garlic, *Allium sativum*, globe artichoke, *Cynara scolymus, Cynara cardunculus* var. *scolymus*, Jerusalem artichoke, *Helianthus tuberosus*, jicama, *Pachyrhizus erosus*, Leopard's bane, *Arnica montana*, mugwort root, *Artemisia vulgaris*, onion, *Allium cepa*, wild yam, *Dioscorea* spp., yacón, *Smallanthus sonchifolius*, and other similar tuberous plants.

After extracting raw inulin, the fractions with degree of polymerization lower than 10 during manufacturing process are removed, to yield the remaining product is high-performance inulin.

The inulin of the present invention under one embodiment has a degree of polymerization of 2 to 60. Under one embodiment, inulin is a high-performance inulin. Under one embodiment, the inulin of the present invention has a degree of polymerization of less than 10.

Inulin may be obtained commercially as Orafti® from Beneo GmbH (Mannheim, Germany), as Frutafit or Frutalose from Sensus (Roosendaal, The Netherlands), as Fibruline® from Cosucra (Warcoing, Belgium), as In-fibre™ from Fenchem Biotek Ltd. (Nanjing, China), as Oliggo-Fiber® from Cargill (Minneapolis, USA).

Inulin is present in the malodor-mitigating oral care composition in an amount that is efficacious to mitigate oral malodor. It has been found that the growth of beneficial oral health-associated bacteria significantly increased in the presence of inulin at all tested concentrations relative to untreated (0% inulin), indicating inulin fermentation.

It has also been determined that the growth of tested oral malodor-associated bacteria in the presence of inulin was parity to untreated at all tested concentrations, indicating lack of inulin fermentation.

Beneficial oral health-associated bacteria include *Streptococcus salivarius, Streptococcus oxalis*, and *Streptococcus sanguinis.*

*Streptococcus salivarius* is one of the first colonizers of the human oral cavity and gut after birth and therefore may contribute to the establishment of immune homeostasis and regulation of host inflammatory responses, making further exposure to the bacteria harmless in most circumstances. It is a species of spherical, gram-positive, facultative anaerobic bacteria that is both catalase and oxidase negative.

*Streptococcus oralis* is a member of the normal human oral microbiota, like related oral streptococci, it exhibits appreciable phenotypic and genetic variation. It is a gram-positive bacterium that grows characteristically in chains, and is found in high numbers in the oral cavity.

*Streptococcus sanguinis* is a gram-positive, facultative anaerobe and a normal inhabitant of the human oral cavity. *S. sanguinis* is a normal inhabitant of the healthy human mouth where it is particularly found in dental plaque, where it modifies the environment to make it less hospitable for other strains of *Streptococcus* that cause cavities, such as *Streptococcus mutans.*

Oral malodor-associated bacteria include *F. nucleatum, V. parvula.*

*Fusobacterium nucleatum* is a bacterium that is commonly found in the dental plaque of humans and is frequently associated with gum disease. It is a key component of periodontal plaque due to its abundance and its ability to coaggregate with other species in the oral cavity. The cells of *F. nucleatum* are fusiform rods or spindle-shaped of many different lengths. In fact, the name refers to the organism as a small spindle-shaped rod. *F. nucleatum* is found in the dental plaque of many primates, thus includes man. This bacteria has been shown to play a central role in dental plaque formation and other diseases like gingivitis. This is due to its ability to adhere to a wide range of both Gram-positive and Gram-negative plaque microorganisms, such as *Porphyromonas gingivalis. F. nucleatum* is very much associated with periodontitis, along with invasive human infections of the head and neck, chest, lung, liver and abdomen. Due to its adherence ability, it can be associated with viruses, which adhere to host tissue cells as an invasion and modulate the host's immune response.

*Veillonella parvula* is a gram negative, strict anaerobic, non-spore-forming coccus-shaped bacterium. It is found in the gut of humans and dental plaque. While considered non-pathogenic, it has been linked with rare cases of meningitis, osteomyelitis, and periodontal disease. It cannot metabolize carbohydrates, but instead uses organic acids like lactate. Perhaps the most significant role of *V. parvula* is its involvement in biofilms. It is able to coaggregate with other organisms, namely *Streptococcus mutans*, to the dental plaque. The two organisms have a mutualistic relationship with each other; *V. parvula* cannot adhere to the surface of teeth by itself, and so attaches to *S. mutans*. It can use the lactate product formed by *S. mutans* for its metabolism, in the process forming a less corrosive acid. In this particular case, the biofilm has been found to be more resistant to antimicrobials than either of the singular species.

Under one embodiment, the malodor-mitigating oral care composition comprises about 0.01 wt % to about 2 wt % of inulin. Under one embodiment, the malodor-mitigating oral care composition comprises about 0.01 wt % to about 1 wt % of inulin. Under one embodiment, the malodor-mitigating oral care composition comprises about 0.01 wt % to about 0.5 wt % of inulin. Under one embodiment, the malodor-mitigating oral care composition comprises about 0.01 wt % to about 0.3 wt % of inulin. Under one embodiment, the malodor-mitigating oral care composition comprises about 0.01 wt % to about 0.1 wt % of inulin. Under one embodiment, the malodor-mitigating oral care composition comprises about 0.01 wt % to about 0.03 wt % of inulin.

Under one embodiment, the malodor-mitigating oral care composition comprises about 0.03 wt % to about 2 wt % of inulin. Under one embodiment, the malodor-mitigating oral care composition comprises about 0.03 wt % to about 1 wt % of inulin. Under one embodiment, the malodor-mitigating oral care composition comprises about 0.03 wt % to about 0.5 wt % of inulin. Under one embodiment, the malodor-mitigating oral care composition comprises about 0.03 wt % to about 0.3 wt % of inulin. Under one embodiment, the malodor-mitigating oral care composition comprises about 0.03 wt % to about 0.1 wt % of inulin. Under one embodiment, the malodor-mitigating oral care composition comprises about 0.1 wt % to about 2 wt % of inulin. Under one embodiment, the malodor-mitigating oral care composition comprises about 0.1 wt % to about 1 wt % of inulin. Under one embodiment, the malodor-mitigating oral care composition comprises about 0.1 wt % to about 0.5 wt % of inulin. Under one embodiment, the malodor-mitigating oral care composition comprises about 0.1 wt % to about 0.3 wt % of inulin.

Under one embodiment, the malodor-mitigating oral care composition comprises about 0.3 wt % to about 2 wt % of inulin. Under one embodiment, the malodor-mitigating oral care composition comprises about 0.3 wt % to about 1 wt % of inulin. Under one embodiment, the malodor-mitigating oral care composition comprises about 0.3 wt % to about 0.5 wt % of inulin. Under one embodiment, the malodor-mitigating oral care composition comprises about 0.5 wt % to about 2 wt % of inulin. Under one embodiment, the malodor-mitigating oral care composition comprises about 0.5 wt % to about 1 wt % of inulin. Under one embodiment, the malodor-mitigating oral care composition comprises about 1 wt % to about 2 wt % of inulin.

Under one embodiment, the malodor-mitigating oral care composition comprises higher formulation dose of inulin to accommodate product dilution during use. This dilution may occur due to the difference between the malodor-mitigating oral care composition, and the oral care product containing such composition.

Further, such dilution may also occur during the use of the oral care product. For example, the oral care product may be diluted by the patient purposefully, in order to, for example, make the product more palatable, or it may be diluted accidently, such as in care that the oral cavity contains large amounts of water or saliva compared to the amount of the oral care product.

Under one embodiment, the malodor-mitigating oral care composition comprises about 1 wt % to about 5 wt % of inulin. Under one embodiment, the malodor-mitigating oral care composition comprises about 1.5 wt % to about 5 wt % of inulin. Under one embodiment, the malodor-mitigating oral care composition comprises about 2 wt % to about 5 wt % of inulin. Under one embodiment, the malodor-mitigating oral care composition comprises about 3 wt % to about 5 wt % of inulin. Under one embodiment, the malodor-mitigating oral care composition comprises about 4 wt % to about 5 wt % of inulin. Under one embodiment, the malodor-mitigating oral care composition comprises about 1 wt % to about 4 wt % of inulin. Under one embodiment, the malodor-mitigating oral care composition comprises about 1.5 wt % to about 4 wt % of inulin. Under one embodiment, the malodor-mitigating oral care composition comprises about 2 wt % to about 4 wt % of inulin.

Under one embodiment, the malodor-mitigating oral care composition comprises about 3 wt % to about 4 wt % of inulin. Under one embodiment, the malodor-mitigating oral care composition comprises about 1 wt % to about 3 wt % of inulin. Under one embodiment, the malodor-mitigating oral care composition comprises about 1.5 wt % to about 3 wt % of inulin. Under one embodiment, the malodor-mitigating oral care composition comprises about 2 wt % to about 3 wt % of inulin. Under one embodiment, the malodor-mitigating oral care composition comprises about 1 wt % to about 2 wt % of inulin. Under one embodiment, the malodor-mitigating oral care composition comprises about 1.5 wt % to about 2 wt % of inulin. Under one embodiment, the malodor-mitigating oral care composition comprises about 1 wt % to about 1.5 wt % of inulin.

The present invention is also directed to an malodor-mitigating oral care composition comprising inulin and further comprising a zinc ion source.

The function of the zinc ion source in the compositions of the present invention is that of a zinc compound to furnish zinc ions. Zinc ion source is a chemical compound, a complex, or a salt that supplies the oral care composition with zinc cations. Zinc ions may be furnished by any physiologically acceptable zinc salt having a measurable solubility in water. The effective portion of the zinc salts are the zinc ions, i.e., zinc cations. The remainder of the molecule of the zinc salt may be inert. Under one embodiment, it is immaterial which of the many possible zinc compounds is used, so long as it is capable of furnishing zinc ions within the range of proportions required by the invention. For purposes of the invention, zinc compounds are considered to be soluble if the compounds are soluble in water to the extent equivalent to at least about 1 gram of Zn per 100 mL of water at about 25° C., and as slightly soluble at lower solubilities. Under one embodiment, it is preferred to use the slightly soluble zinc compounds. Under one embodiment, the zinc ion source is a soluble salt.

Examples of zinc ion source includes zinc sulfate, zinc chloride, zinc acetate, zinc phenolsulfonate, zinc borate, zinc bromide, zinc nitrate, zinc glycerophosphate, zinc benzoate, zinc carbonate, zinc citrate, zinc hexafluorosilicate, zinc lactate trihydrate, zinc oxide, zinc peroxide, zinc salicylate, zinc silicate, zinc soaps of fatty acids having 8-18 carbon atoms, zinc stannate, zinc tannate, zinc tartrate, zinc titanate, zinc tetrafluoroborate, and mixtures thereof.

The present invention is also directed to an malodor-mitigating oral care composition comprising inulin and further comprising a zinc ion source, wherein the zinc ion source is selected from the group consisting of zinc oxide, ZnO, zinc sulfate, $ZnSO_4$, zinc chloride, $ZnCl_2$, zinc citrate, $C_{12}H_{10}O_{14}Zn_3$, zinc lactate, $C_6H_{10}O_6Zn$, zinc gluconate, $C_{12}H_{22}O_{14}Zn$, zinc malate, $C_4H_4O_5Zn$, zinc tartrate, $C_4H_4O_6Zn$, zinc carbonate, $ZnCO_3$, zinc phosphate, $Zn_3(PO_4)_2$, and mixtures thereof.

The zinc ion source may further be a hydrate. Thus, for example, the phrase "zinc phosphate" not only refers to the composition of $Zn_3(PO_4)_2$, but also to the hydrates, such as, $Zn_3(PO_4)_2 \cdot x(H_2O)$, or $Zn_3(PO_4)_2(H_2O)_n$, wherein the x is number between 0 to 4. The number of water molecules per zinc salt may be an integer, a fraction, or any number less then 10. Examples include monohydrates, dehydrates, trihydrates, tetrahydrates, and pentahydrates.

The present invention is also directed to an malodor-mitigating oral care composition comprising inulin, a zinc ion source, and a humectant.

The humectant of the present invention is a hygroscopic substance used to keep the oral care composition moist. Under one embodiment, it is often a molecule with several hydrophilic groups, such as hydroxyl, amine and carboxyl groups. The carboxylic groups may be esterified. The humectant used in the present invention is similar to those used in personal care products, oral care products, foods, cosmetics, medicines and pesticides.

Further, the term "humectant", for the purposes of present invention, includes edible polyhydric alcohols such as glycerin, sorbitol, xylitol, butylene glycol, propylene glycol, and combinations thereof. Under one embodiment, the humectant is a polyol. Such a polyol may be selected from sorbitol, glycerin, and combinations thereof. In yet another embodiment, the humectant is xylitol.

More specifically, the present invention is also directed to an malodor-mitigating oral care composition comprising inulin, a zinc ion source, and a humectant selected from the group consisting of glycerin, sorbitol, xylitol, butylene glycol, polyethylene glycol, propylene glycol, trimethyl glycine, and mixtures thereof. Under one embodiment, the present invention is also directed to an malodor-mitigating oral care composition comprising inulin, a zinc ion source, and xylitol.

Under one embodiment, the malodor-mitigating oral care composition comprises inulin, humectant and zinc ion source, wherein the weight ratio of inulin:humectant:zinc ion from zinc ion source is 5 to 50:5 to 50:1 to 10. Under one embodiment, the malodor-mitigating oral care composition comprises inulin, humectant and zinc ion source, wherein the weight ratio of inulin:humectant:zinc ion from zinc ion source is 10 to 50:5 to 50:1 to 10. Under one embodiment, the malodor-mitigating oral care composition comprises inulin, humectant and zinc ion source, wherein the weight ratio of inulin:humectant:zinc ion from zinc ion source is 20 to 50:5 to 50:1 to 10. Under one embodiment, the malodor-mitigating oral care composition comprises inulin, humectant and zinc ion source, wherein the weight ratio of inulin:humectant:zinc ion from zinc ion source is 30 to 50:5 to 50:1 to 10. Under one embodiment, the malodor-mitigating oral care composition comprises inulin, humectant and zinc ion source, wherein the weight ratio of inulin:humectant:zinc ion from zinc ion source is 40 to 50:5 to 50:1 to 10.

Under one embodiment, the malodor-mitigating oral care composition comprises inulin, humectant and zinc ion source, wherein the weight ratio of inulin:humectant:zinc ion from zinc ion source is 5 to 40:5 to 50:0.5 to 10. Under one embodiment, the malodor-mitigating oral care composition comprises inulin, humectant and zinc ion source, wherein the weight ratio of inulin:humectant:zinc ion from zinc ion source is 10 to 40:5 to 50:1 to 10. Under one embodiment, the malodor-mitigating oral care composition comprises inulin, humectant and zinc ion source, wherein the weight ratio of inulin:humectant:zinc ion from zinc ion source is 20 to 40:5 to 50:1 to 10. Under one embodiment, the malodor-mitigating oral care composition comprises inulin, humectant and zinc ion source, wherein the weight ratio of inulin:humectant:zinc ion from zinc ion source is 30 to 40:5 to 50:1 to 10.

Under one embodiment, the malodor-mitigating oral care composition comprises inulin, humectant and zinc ion source, wherein the weight ratio of inulin:humectant:zinc ion from zinc ion source is 5 to 30:5 to 50:0.5 to 10. Under one embodiment, the malodor-mitigating oral care composition comprises inulin, humectant and zinc ion source, wherein the weight ratio of inulin:humectant:zinc ion from zinc ion source is 10 to 30:5 to 50:1 to 10. Under one embodiment, the malodor-mitigating oral care composition comprises inulin, humectant and zinc ion source, wherein the weight ratio of inulin:humectant:zinc ion from zinc ion source is 20 to 30:5 to 50:1 to 10.

Under one embodiment, the malodor-mitigating oral care composition comprises inulin, humectant and zinc ion source, wherein the weight ratio of inulin:humectant:zinc ion from zinc ion source is 5 to 20:5 to 50:0.5 to 10. Under one embodiment, the malodor-mitigating oral care composition comprises inulin, humectant and zinc ion source, wherein the weight ratio of inulin:humectant:zinc ion from zinc ion source is 10 to 20:5 to 50:1 to 10. Under one embodiment, the malodor-mitigating oral care composition comprises inulin, humectant and zinc ion source, wherein the weight ratio of inulin:humectant:zinc ion from zinc ion source is 5 to 10:5 to 50:0.5 to 10.

Under one embodiment, the malodor-mitigating oral care composition comprises inulin, humectant and zinc ion source, wherein the weight ratio of inulin:humectant:zinc ion from zinc ion source is 5 to 50:5 to 40:0.5 to 10. Under one embodiment, the malodor-mitigating oral care composition comprises inulin, humectant and zinc ion source, wherein the weight ratio of inulin:humectant:zinc ion from zinc ion source is 10 to 50:5 to 40:1 to 10. Under one embodiment, the malodor-mitigating oral care composition comprises inulin, humectant and zinc ion source, wherein the weight ratio of inulin:humectant:zinc ion from zinc ion source is 20 to 50:5 to 40:1 to 10. Under one embodiment, the malodor-mitigating oral care composition comprises inulin, humectant and zinc ion source, wherein the weight ratio of inulin:humectant:zinc ion from zinc ion source is 30 to 50:5 to 40:1 to 10. Under one embodiment, the malodor-mitigating oral care composition comprises inulin, humectant and zinc ion source, wherein the weight ratio of inulin:humectant:zinc ion from zinc ion source is 40 to 50:5 to 40:1 to 10.

Under one embodiment, the malodor-mitigating oral care composition comprises inulin, humectant and zinc ion source, wherein the weight ratio of inulin:humectant:zinc ion from zinc ion source is 5 to 40:5 to 40:0.5 to 10. Under one embodiment, the malodor-mitigating oral care composition comprises inulin, humectant and zinc ion source, wherein the weight ratio of inulin:humectant:zinc ion from zinc ion source is 10 to 40:5 to 40:1 to 10. Under one embodiment, the malodor-mitigating oral care composition comprises inulin, humectant and zinc ion source, wherein the weight ratio of inulin:humectant:zinc ion from zinc ion source is 20 to 40:5 to 40:1 to 10. Under one embodiment, the malodor-mitigating oral care composition comprises inulin, humectant and zinc ion source, wherein the weight ratio of inulin:humectant:zinc ion from zinc ion source is 30 to 40:5 to 40:1 to 10.

Under one embodiment, the malodor-mitigating oral care composition comprises inulin, humectant and zinc ion source, wherein the weight ratio of inulin:humectant:zinc ion from zinc ion source is 5 to 30:5 to 40:0.5 to 10. Under one embodiment, the malodor-mitigating oral care composition comprises inulin, humectant and zinc ion source, wherein the weight ratio of inulin:humectant:zinc ion from zinc ion source is 10 to 30:5 to 40:1 to 10. Under one embodiment, the malodor-mitigating oral care composition comprises inulin, humectant and zinc ion source, wherein the weight ratio of inulin:humectant:zinc ion from zinc ion source is 20 to 30:5 to 40:1 to 10.

Under one embodiment, the malodor-mitigating oral care composition comprises inulin, humectant and zinc ion source, wherein the weight ratio of inulin:humectant:zinc ion from zinc ion source is 5 to 20:5 to 40:0.5 to 10. Under one embodiment, the malodor-mitigating oral care composition comprises inulin, humectant and zinc ion source, wherein the weight ratio of inulin:humectant:zinc ion from zinc ion source is 10 to 20:5 to 40:1 to 10. Under one embodiment, the malodor-mitigating oral care composition comprises inulin, humectant and zinc ion source, wherein the weight ratio of inulin:humectant:zinc ion from zinc ion source is 5 to 10:5 to 40:0.5 to 10.

Under one embodiment, the malodor-mitigating oral care composition comprises inulin, humectant and zinc ion source, wherein the weight ratio of inulin:humectant:zinc ion from zinc ion source is 5 to 50:5 to 30:0.5 to 10. Under one embodiment, the malodor-mitigating oral care composition comprises inulin, humectant and zinc ion source, wherein the weight ratio of inulin:humectant:zinc ion from zinc ion source is 10 to 50:5 to 30:1 to 10. Under one embodiment, the malodor-mitigating oral care composition comprises inulin, humectant and zinc ion source, wherein the weight ratio of inulin:humectant:zinc ion from zinc ion source is 20 to 50:5 to 30:1 to 10. Under one embodiment, the malodor-mitigating oral care composition comprises inulin, humectant and zinc ion source, wherein the weight ratio of inulin:humectant:zinc ion from zinc ion source is 30 to 50:5 to 30:1 to 10. Under one embodiment, the malodor-mitigating oral care composition comprises inulin, humectant and zinc ion source, wherein the weight ratio of inulin:humectant:zinc ion from zinc ion source is 40 to 50:5 to 30:1 to 10.

Under one embodiment, the malodor-mitigating oral care composition comprises inulin, humectant and zinc ion source, wherein the weight ratio of inulin:humectant:zinc ion from zinc ion source is 5 to 40:5 to 30:0.5 to 10. Under one embodiment, the malodor-mitigating oral care composition comprises inulin, humectant and zinc ion source, wherein the weight ratio of inulin:humectant:zinc ion from zinc ion source is 10 to 40:5 to 30:1 to 10. Under one embodiment, the malodor-mitigating oral care composition comprises inulin, humectant and zinc ion source, wherein the weight ratio of inulin:humectant:zinc ion from zinc ion source is 20 to 40:5 to 30:1 to 10. Under one embodiment, the malodor-mitigating oral care composition comprises inulin, humectant and zinc ion source, wherein the weight ratio of inulin:humectant:zinc ion from zinc ion source is 30 to 40:5 to 30:1 to 10.

Under one embodiment, the malodor-mitigating oral care composition comprises inulin, humectant and zinc ion source, wherein the weight ratio of inulin:humectant:zinc ion from zinc ion source is 5 to 30:5 to 30:0.5 to 10. Under one embodiment, the malodor-mitigating oral care composition comprises inulin, humectant and zinc ion source, wherein the weight ratio of inulin:humectant:zinc ion from zinc ion source is 10 to 30:5 to 30:1 to 10. Under one embodiment, the malodor-mitigating oral care composition comprises inulin, humectant and zinc ion source, wherein the weight ratio of inulin:humectant:zinc ion from zinc ion source is 20 to 30:5 to 30:1 to 10.

Under one embodiment, the malodor-mitigating oral care composition comprises inulin, humectant and zinc ion source, wherein the weight ratio of inulin:humectant:zinc ion from zinc ion source is 5 to 20:5 to 30:0.5 to 10. Under one embodiment, the malodor-mitigating oral care composition comprises inulin, humectant and zinc ion source, wherein the weight ratio of inulin:humectant:zinc ion from zinc ion source is 10 to 20:5 to 30:1 to 10. Under one embodiment, the malodor-mitigating oral care composition comprises inulin, humectant and zinc ion source, wherein the weight ratio of inulin:humectant:zinc ion from zinc ion source is 5 to 10:5 to 30:0.5 to 10.

Under one embodiment, the malodor-mitigating oral care composition comprises inulin, humectant and zinc ion source, wherein the weight ratio of inulin:humectant:zinc ion from zinc ion source is 5 to 50:5 to 20:0.5 to 10. Under one embodiment, the malodor-mitigating oral care composition comprises inulin, humectant and zinc ion source, wherein the weight ratio of inulin:humectant:zinc ion from zinc ion source is 10 to 50:5 to 20:1 to 10. Under one embodiment, the malodor-mitigating oral care composition comprises inulin, humectant and zinc ion source, wherein the weight ratio of inulin:humectant:zinc ion from zinc ion source is 20 to 50:5 to 20:1 to 10. Under one embodiment, the malodor-mitigating oral care composition comprises inulin, humectant and zinc ion source, wherein the weight ratio of inulin:humectant:zinc ion from zinc ion source is 30 to 50:5 to 20:1 to 10. Under one embodiment, the malodor-mitigating oral care composition comprises inulin, humectant and zinc ion source, wherein the weight ratio of inulin:humectant:zinc ion from zinc ion source is 40 to 50:5 to 20:1 to 10.

Under one embodiment, the malodor-mitigating oral care composition comprises inulin, humectant and zinc ion source, wherein the weight ratio of inulin:humectant:zinc ion from zinc ion source is 5 to 40:5 to 20:0.5 to 10. Under one embodiment, the malodor-mitigating oral care composition comprises inulin, humectant and zinc ion source, wherein the weight ratio of inulin:humectant:zinc ion from zinc ion source is 10 to 40:5 to 20:1 to 10. Under one embodiment, the malodor-mitigating oral care composition comprises inulin, humectant and zinc ion source, wherein the weight ratio of inulin:humectant:zinc ion from zinc ion source is 20 to 40:5 to 20:1 to 10. Under one embodiment, the malodor-mitigating oral care composition comprises inulin, humectant and zinc ion source, wherein the weight ratio of inulin:humectant:zinc ion from zinc ion source is 30 to 40:5 to 20:1 to 10.

Under one embodiment, the malodor-mitigating oral care composition comprises inulin, humectant and zinc ion source, wherein the weight ratio of inulin:humectant:zinc ion from zinc ion source is 5 to 30:5 to 20:0.5 to 10. Under one embodiment, the malodor-mitigating oral care composition comprises inulin, humectant and zinc ion source, wherein the weight ratio of inulin:humectant:zinc ion from zinc ion source is 10 to 30:5 to 20:1 to 10. Under one embodiment, the malodor-mitigating oral care composition comprises inulin, humectant and zinc ion source, wherein the weight ratio of inulin:humectant:zinc ion from zinc ion source is 20 to 30:5 to 20:1 to 10.

Under one embodiment, the malodor-mitigating oral care composition comprises inulin, humectant and zinc ion source, wherein the weight ratio of inulin:humectant:zinc ion from zinc ion source is 5 to 20:5 to 20:0.5 to 10. Under one embodiment, the malodor-mitigating oral care composition comprises inulin, humectant and zinc ion source, wherein the weight ratio of inulin:humectant:zinc ion from zinc ion source is 10 to 20:5 to 20:1 to 10. Under one embodiment, the malodor-mitigating oral care composition comprises inulin, humectant and zinc ion source, wherein the weight ratio of inulin:humectant:zinc ion from zinc ion source is 5 to 10:5 to 20:0.5 to 10.

Under one embodiment, the malodor-mitigating oral care composition comprises inulin, humectant and zinc ion source, wherein the weight ratio of inulin:humectant:zinc ion from zinc ion source is 5 to 50:5 to 10:0.5 to 10. Under one embodiment, the malodor-mitigating oral care composition comprises inulin, humectant and zinc ion source, wherein the weight ratio of inulin:humectant:zinc ion from zinc ion source is 10 to 50:5 to 10:1 to 10. Under one embodiment, the malodor-mitigating oral care composition comprises inulin, humectant and zinc ion source, wherein the weight ratio of inulin:humectant:zinc ion from zinc ion source is 20 to 50:5 to 10:1 to 10. Under one embodiment, the malodor-mitigating oral care composition comprises inulin, humectant and zinc ion source, wherein the weight ratio of inulin:humectant:zinc ion from zinc ion source is 30 to 50:5 to 10:1 to 10. Under one embodiment, the malodor-mitigating oral care composition comprises inulin, humectant and zinc ion source, wherein the weight ratio of inulin:humectant:zinc ion from zinc ion source is 40 to 50:5 to 10:1 to 10.

Under one embodiment, the malodor-mitigating oral care composition comprises inulin, humectant and zinc ion source, wherein the weight ratio of inulin:humectant:zinc ion from zinc ion source is 5 to 40:5 to 10:0.5 to 10. Under one embodiment, the malodor-mitigating oral care composition comprises inulin, humectant and zinc ion source, wherein the weight ratio of inulin:humectant:zinc ion from zinc ion source is 10 to 40:5 to 10:1 to 10. Under one embodiment, the malodor-mitigating oral care composition comprises inulin, humectant and zinc ion source, wherein the weight ratio of inulin:humectant:zinc ion from zinc ion source is 20 to 40:5 to 10:1 to 10. Under one embodiment, the malodor-mitigating oral care composition comprises inulin, humectant and zinc ion source, wherein the weight ratio of inulin:humectant:zinc ion from zinc ion source is 30 to 40:5 to 10:1 to 10.

Under one embodiment, the malodor-mitigating oral care composition comprises inulin, humectant and zinc ion source, wherein the weight ratio of inulin:humectant:zinc ion from zinc ion source is 5 to 30:5 to 10:0.5 to 10. Under one embodiment, the malodor-mitigating oral care composition comprises inulin, humectant and zinc ion source, wherein the weight ratio of inulin:humectant:zinc ion from zinc ion source is 10 to 30:5 to 10:1 to 10. Under one embodiment, the malodor-mitigating oral care composition comprises inulin, humectant and zinc ion source, wherein the weight ratio of inulin:humectant:zinc ion from zinc ion source is 20 to 30:5 to 10:1 to 10.

Under one embodiment, the malodor-mitigating oral care composition comprises inulin, humectant and zinc ion source, wherein the weight ratio of inulin:humectant:zinc ion from zinc ion source is 5 to 20:5 to 10:0.5 to 10. Under one embodiment, the malodor-mitigating oral care composition comprises inulin, humectant and zinc ion source, wherein the weight ratio of inulin:humectant:zinc ion from zinc ion source is 10 to 20:5 to 10:1 to 10. Under one embodiment, the malodor-mitigating oral care composition comprises inulin, humectant and zinc ion source, wherein the weight ratio of inulin:humectant:zinc ion from zinc ion source is 5 to 10:5 to 10:0.5 to 10.

Under one embodiment, the malodor-mitigating oral care composition comprises inulin, humectant and zinc ion source, wherein the weight ratio of inulin:humectant:zinc ion from zinc ion source is 5 to 50:10 to 50:0.5 to 10. Under one embodiment, the malodor-mitigating oral care composition comprises inulin, humectant and zinc ion source, wherein the weight ratio of inulin:humectant:zinc ion from zinc ion source is 10 to 50:10 to 50:1 to 10. Under one embodiment, the malodor-mitigating oral care composition comprises inulin, humectant and zinc ion source, wherein the weight ratio of inulin:humectant:zinc ion from zinc ion source is 20 to 50:10 to 50:1 to 10. Under one embodiment, the malodor-mitigating oral care composition comprises inulin, humectant and zinc ion source, wherein the weight ratio of inulin:humectant:zinc ion from zinc ion source is 30 to 50:10 to 50:1 to 10. Under one embodiment, the malodor-mitigating oral care composition comprises inulin, humectant and zinc ion source, wherein the weight ratio of inulin:humectant:zinc ion from zinc ion source is 40 to 50:10 to 50:1 to 10.

Under one embodiment, the malodor-mitigating oral care composition comprises inulin, humectant and zinc ion source, wherein the weight ratio of inulin:humectant:zinc ion from zinc ion source is 5 to 40:10 to 50:0.5 to 10. Under one embodiment, the malodor-mitigating oral care composition comprises inulin, humectant and zinc ion source, wherein the weight ratio of inulin:humectant:zinc ion from zinc ion source is 10 to 40:10 to 50:1 to 10. Under one embodiment, the malodor-mitigating oral care composition comprises inulin, humectant and zinc ion source, wherein the weight ratio of inulin:humectant:zinc ion from zinc ion source is 20 to 40:10 to 50:1 to 10. Under one embodiment, the malodor-mitigating oral care composition comprises inulin, humectant and zinc ion source, wherein the weight ratio of inulin:humectant:zinc ion from zinc ion source is 30 to 40:10 to 50:1 to 10.

Under one embodiment, the malodor-mitigating oral care composition comprises inulin, humectant and zinc ion source, wherein the weight ratio of inulin:humectant:zinc ion from zinc ion source is 5 to 30:10 to 50:0.5 to 10. Under one embodiment, the malodor-mitigating oral care composition comprises inulin, humectant and zinc ion source, wherein the weight ratio of inulin:humectant:zinc ion from zinc ion source is 10 to 30:10 to 50:1 to 10. Under one embodiment, the malodor-mitigating oral care composition comprises inulin, humectant and zinc ion source, wherein the weight ratio of inulin:humectant:zinc ion from zinc ion source is 20 to 30:10 to 50:1 to 10.

Under one embodiment, the malodor-mitigating oral care composition comprises inulin, humectant and zinc ion source, wherein the weight ratio of inulin:humectant:zinc ion from zinc ion source is 5 to 20:10 to 50:0.5 to 10. Under one embodiment, the malodor-mitigating oral care composition comprises inulin, humectant and zinc ion source, wherein the weight ratio of inulin:humectant:zinc ion from zinc ion source is 10 to 20:10 to 50:1 to 10. Under one embodiment, the malodor-mitigating oral care composition comprises inulin, humectant and zinc ion source, wherein the weight ratio of inulin:humectant:zinc ion from zinc ion source is 5 to 10:10 to 50:0.5 to 10.

Under one embodiment, the malodor-mitigating oral care composition comprises inulin, humectant and zinc ion source, wherein the weight ratio of inulin:humectant:zinc ion from zinc ion source is 5 to 50:10 to 40:0.5 to 10. Under one embodiment, the malodor-mitigating oral care composition comprises inulin, humectant and zinc ion source, wherein the weight ratio of inulin:humectant:zinc ion from zinc ion source is 10 to 40:10 to 50:1 to 10. Under one embodiment, the malodor-mitigating oral care composition comprises inulin, humectant and zinc ion source, wherein the weight ratio of inulin:humectant:zinc ion from zinc ion source is 20 to 50:10 to 40:1 to 10. Under one embodiment, the malodor-mitigating oral care composition comprises inulin, humectant and zinc ion source, wherein the weight ratio of inulin:humectant:zinc ion from zinc ion source is 30 to 50:10 to 40:1 to 10. Under one embodiment, the malodor-mitigating oral care composition comprises inulin, humectant and zinc ion source, wherein the weight ratio of inulin:humectant:zinc ion from zinc ion source is 40 to 50:10 to 40:1 to 10.

Under one embodiment, the malodor-mitigating oral care composition comprises inulin, humectant and zinc ion source, wherein the weight ratio of inulin:humectant:zinc ion from zinc ion source is 5 to 40:10 to 40:0.5 to 10. Under one embodiment, the malodor-mitigating oral care composition comprises inulin, humectant and zinc ion source, wherein the weight ratio of inulin:humectant:zinc ion from zinc ion source is 10 to 40:10 to 40:1 to 10. Under one embodiment, the malodor-mitigating oral care composition comprises inulin, humectant and zinc ion source, wherein the weight ratio of inulin:humectant:zinc ion from zinc ion source is 20 to 40:10 to 40:1 to 10. Under one embodiment, the malodor-mitigating oral care composition comprises inulin, humectant and zinc ion source, wherein the weight ratio of inulin:humectant:zinc ion from zinc ion source is 30 to 40:10 to 40:1 to 10.

Under one embodiment, the malodor-mitigating oral care composition comprises inulin, humectant and zinc ion source, wherein the weight ratio of inulin:humectant:zinc ion from zinc ion source is 5 to 30:10 to 40:0.5 to 10. Under one embodiment, the malodor-mitigating oral care composition comprises inulin, humectant and zinc ion source, wherein the weight ratio of inulin:humectant:zinc ion from zinc ion source is 10 to 30:10 to 40:1 to 10. Under one embodiment, the malodor-mitigating oral care composition comprises inulin, humectant and zinc ion source, wherein the weight ratio of inulin:humectant:zinc ion from zinc ion source is 20 to 30:10 to 40:1 to 10.

Under one embodiment, the malodor-mitigating oral care composition comprises inulin, humectant and zinc ion source, wherein the weight ratio of inulin:humectant:zinc ion from zinc ion source is 5 to 20:10 to 40:0.5 to 10. Under one embodiment, the malodor-mitigating oral care composition comprises inulin, humectant and zinc ion source, wherein the weight ratio of inulin:humectant:zinc ion from zinc ion source is 10 to 20:10 to 40:1 to 10. Under one embodiment, the malodor-mitigating oral care composition comprises inulin, humectant and zinc ion source, wherein the weight ratio of inulin:humectant:zinc ion from zinc ion source is 5 to 10:10 to 40:0.5 to 10.

Under one embodiment, the malodor-mitigating oral care composition comprises inulin, humectant and zinc ion source, wherein the weight ratio of inulin:humectant:zinc ion from zinc ion source is 5 to 50:10 to 30:0.5 to 10. Under one embodiment, the malodor-mitigating oral care composition comprises inulin, humectant and zinc ion source, wherein the weight ratio of inulin:humectant:zinc ion from zinc ion source is 10 to 30:10 to 50:1 to 10. Under one embodiment, the malodor-mitigating oral care composition comprises inulin, humectant and zinc ion source, wherein the weight ratio of inulin:humectant:zinc ion from zinc ion source is 20 to 50:10 to 30:1 to 10. Under one embodiment, the malodor-mitigating oral care composition comprises inulin, humectant and zinc ion source, wherein the weight ratio of inulin:humectant:zinc ion from zinc ion source is 30 to 50:10 to 30:1 to 10. Under one embodiment, the malodor-mitigating oral care composition comprises inulin, humectant and zinc ion source, wherein the weight ratio of inulin:humectant:zinc ion from zinc ion source is 40 to 50:10 to 30:1 to 10.

Under one embodiment, the malodor-mitigating oral care composition comprises inulin, humectant and zinc ion source, wherein the weight ratio of inulin:humectant:zinc ion from zinc ion source is 5 to 40:10 to 30:0.5 to 10. Under one embodiment, the malodor-mitigating oral care composition comprises inulin, humectant and zinc ion source, wherein the weight ratio of inulin:humectant:zinc ion from zinc ion source is 10 to 30:10 to 40:1 to 10. Under one embodiment, the malodor-mitigating oral care composition comprises inulin, humectant and zinc ion source, wherein the weight ratio of inulin:humectant:zinc ion from zinc ion source is 20 to 40:10 to 30:1 to 10. Under one embodiment, the malodor-mitigating oral care composition comprises inulin, humectant and zinc ion source, wherein the weight ratio of inulin:humectant:zinc ion from zinc ion source is 30 to 40:10 to 30:1 to 10.

Under one embodiment, the malodor-mitigating oral care composition comprises inulin, humectant and zinc ion source, wherein the weight ratio of inulin:humectant:zinc ion from zinc ion source is 5 to 30:10 to 30:0.5 to 10. Under one embodiment, the malodor-mitigating oral care composition comprises inulin, humectant and zinc ion source, wherein the weight ratio of inulin:humectant:zinc ion from zinc ion source is 10 to 30:10 to 30:1 to 10. Under one embodiment, the malodor-mitigating oral care composition comprises inulin, humectant and zinc ion source, wherein the weight ratio of inulin:humectant:zinc ion from zinc ion source is 20 to 30:10 to 30:1 to 10.

Under one embodiment, the malodor-mitigating oral care composition comprises inulin, humectant and zinc ion source, wherein the weight ratio of inulin:humectant:zinc ion from zinc ion source is 5 to 20:10 to 30:0.5 to 10. Under one embodiment, the malodor-mitigating oral care composition comprises inulin, humectant and zinc ion source, wherein the weight ratio of inulin:humectant:zinc ion from zinc ion source is 10 to 20:10 to 30:1 to 10. Under one embodiment, the malodor-mitigating oral care composition comprises inulin, humectant and zinc ion source, wherein the weight ratio of inulin:humectant:zinc ion from zinc ion source is 5 to 10:10 to 30:0.5 to 10.

Under one embodiment, the malodor-mitigating oral care composition comprises inulin, humectant and zinc ion source, wherein the weight ratio of inulin:humectant:zinc ion from zinc ion source is 5 to 50:10 to 20:0.5 to 10. Under one embodiment, the malodor-mitigating oral care composition comprises inulin, humectant and zinc ion source, wherein the weight ratio of inulin:humectant:zinc ion from zinc ion source is 10 to 20:10 to 50:1 to 10. Under one embodiment, the malodor-mitigating oral care composition comprises inulin, humectant and zinc ion source, wherein the weight ratio of inulin:humectant:zinc ion from zinc ion source is 20 to 50:10 to 20:1 to 10. Under one embodiment, the malodor-mitigating oral care composition comprises inulin, humectant and zinc ion source, wherein the weight ratio of inulin:humectant:zinc ion from zinc ion source is 30 to 50:10 to 20:1 to 10. Under one embodiment, the malodor-mitigating oral care composition comprises inulin, humectant and zinc ion source, wherein the weight ratio of inulin:humectant:zinc ion from zinc ion source is 40 to 50:10 to 20:1 to 10.

Under one embodiment, the malodor-mitigating oral care composition comprises inulin, humectant and zinc ion source, wherein the weight ratio of inulin:humectant:zinc ion from zinc ion source is 5 to 40:10 to 20:0.5 to 10. Under one embodiment, the malodor-mitigating oral care composition comprises inulin, humectant and zinc ion source, wherein the weight ratio of inulin:humectant:zinc ion from zinc ion source is 10 to 20:10 to 40:1 to 10. Under one embodiment, the malodor-mitigating oral care composition comprises inulin, humectant and zinc ion source, wherein the weight ratio of inulin:humectant:zinc ion from zinc ion source is 20 to 40:10 to 20:1 to 10. Under one embodiment, the malodor-mitigating oral care composition comprises inulin, humectant and zinc ion source, wherein the weight ratio of inulin:humectant:zinc ion from zinc ion source is 30 to 40:10 to 20:1 to 10.

Under one embodiment, the malodor-mitigating oral care composition comprises inulin, humectant and zinc ion source, wherein the weight ratio of inulin:humectant:zinc ion from zinc ion source is 5 to 30:10 to 20:0.5 to 10. Under one embodiment, the malodor-mitigating oral care composition comprises inulin, humectant and zinc ion source, wherein the weight ratio of inulin:humectant:zinc ion from zinc ion source is 10 to 20:10 to 30:1 to 10. Under one embodiment, the malodor-mitigating oral care composition comprises inulin, humectant and zinc ion source, wherein the weight ratio of inulin:humectant:zinc ion from zinc ion source is 20 to 30:10 to 20:1 to 10.

Under one embodiment, the malodor-mitigating oral care composition comprises inulin, humectant and zinc ion source, wherein the weight ratio of inulin:humectant:zinc ion from zinc ion source is 5 to 20:10 to 20:0.5 to 10. Under one embodiment, the malodor-mitigating oral care composition comprises inulin, humectant and zinc ion source, wherein the weight ratio of inulin:humectant:zinc ion from zinc ion source is 10 to 20:10 to 20:1 to 10. Under one embodiment, the malodor-mitigating oral care composition comprises inulin, humectant and zinc ion source, wherein the weight ratio of inulin:humectant:zinc ion from zinc ion source is 5 to 10:10 to 20:0.5 to 10.

Under one embodiment, the malodor-mitigating oral care composition comprises inulin, humectant and zinc ion source, wherein the weight ratio of inulin:humectant:zinc ion from zinc ion source is 5 to 50:20 to 50:0.5 to 10. Under one embodiment, the malodor-mitigating oral care composition comprises inulin, humectant and zinc ion source, wherein the weight ratio of inulin:humectant:zinc ion from zinc ion source is 20 to 50:10 to 50:1 to 10. Under one embodiment, the malodor-mitigating oral care composition comprises inulin, humectant and zinc ion source, wherein the weight ratio of inulin:humectant:zinc ion from zinc ion source is 20 to 50:20 to 50:1 to 10. Under one embodiment, the malodor-mitigating oral care composition comprises inulin, humectant and zinc ion source, wherein the weight ratio of inulin:humectant:zinc ion from zinc ion source is 30 to 50:20 to 50:1 to 10. Under one embodiment, the malodor-mitigating oral care composition comprises inulin, humectant and zinc ion source, wherein the weight ratio of inulin:humectant:zinc ion from zinc ion source is 40 to 50:20 to 50:1 to 10.

Under one embodiment, the malodor-mitigating oral care composition comprises inulin, humectant and zinc ion source, wherein the weight ratio of inulin:humectant:zinc ion from zinc ion source is 5 to 40:20 to 50:0.5 to 10. Under one embodiment, the malodor-mitigating oral care composition comprises inulin, humectant and zinc ion source, wherein the weight ratio of inulin:humectant:zinc ion from zinc ion source is 20 to 50:10 to 40:1 to 10. Under one embodiment, the malodor-mitigating oral care composition comprises inulin, humectant and zinc ion source, wherein the weight ratio of inulin:humectant:zinc ion from zinc ion source is 20 to 40:20 to 50:1 to 10. Under one embodiment, the malodor-mitigating oral care composition comprises inulin, humectant and zinc ion source, wherein the weight ratio of inulin:humectant:zinc ion from zinc ion source is 30 to 40:20 to 50:1 to 10.

Under one embodiment, the malodor-mitigating oral care composition comprises inulin, humectant and zinc ion source, wherein the weight ratio of inulin:humectant:zinc ion from zinc ion source is 5 to 30:20 to 50:0.5 to 10. Under one embodiment, the malodor-mitigating oral care composition comprises inulin, humectant and zinc ion source, wherein the weight ratio of inulin:humectant:zinc ion from zinc ion source is 20 to 50:10 to 30:1 to 10. Under one embodiment, the malodor-mitigating oral care composition comprises inulin, humectant and zinc ion source, wherein the weight ratio of inulin:humectant:zinc ion from zinc ion source is 20 to 30:20 to 50:1 to 10.

Under one embodiment, the malodor-mitigating oral care composition comprises inulin, humectant and zinc ion source, wherein the weight ratio of inulin:humectant:zinc ion from zinc ion source is 5 to 20:20 to 50:0.5 to 10. Under one embodiment, the malodor-mitigating oral care composition comprises inulin, humectant and zinc ion source, wherein the weight ratio of inulin:humectant:zinc ion from zinc ion source is 20 to 50:10 to 20:1 to 10. Under one embodiment, the malodor-mitigating oral care composition comprises inulin, humectant and zinc ion source, wherein the weight ratio of inulin:humectant:zinc ion from zinc ion source is 5 to 10:20 to 50:1 to 10.

Under one embodiment, the malodor-mitigating oral care composition comprises inulin, humectant and zinc ion source, wherein the weight ratio of inulin:humectant:zinc ion from zinc ion source is 5 to 50:20 to 40:0.5 to 10. Under one embodiment, the malodor-mitigating oral care composition comprises inulin, humectant and zinc ion source, wherein the weight ratio of inulin:humectant:zinc ion from zinc ion source is 20 to 40:10 to 50:1 to 10. Under one embodiment, the malodor-mitigating oral care composition comprises inulin, humectant and zinc ion source, wherein the weight ratio of inulin:humectant:zinc ion from zinc ion source is 20 to 50:20 to 40:1 to 10. Under one embodiment, the malodor-mitigating oral care composition comprises inulin, humectant and zinc ion source, wherein the weight ratio of inulin:humectant:zinc ion from zinc ion source is 30 to 50:20 to 40:1 to 10. Under one embodiment, the malodor-mitigating oral care composition comprises inulin, humectant and zinc ion source, wherein the weight ratio of inulin:humectant:zinc ion from zinc ion source is 40 to 50:20 to 40:1 to 10.

Under one embodiment, the malodor-mitigating oral care composition comprises inulin, humectant and zinc ion source, wherein the weight ratio of inulin:humectant:zinc ion from zinc ion source is 5 to 40:20 to 40:0.5 to 10. Under one embodiment, the malodor-mitigating oral care composition comprises inulin, humectant and zinc ion source, wherein the weight ratio of inulin:humectant:zinc ion from zinc ion source is 20 to 40:10 to 40:1 to 10. Under one embodiment, the malodor-mitigating oral care composition comprises inulin, humectant and zinc ion source, wherein the weight ratio of inulin:humectant:zinc ion from zinc ion source is 20 to 40:20 to 40:1 to 10. Under one embodiment, the malodor-mitigating oral care composition comprises inulin, humectant and zinc ion source, wherein the weight ratio of inulin:humectant:zinc ion from zinc ion source is 30 to 40:20 to 40:1 to 10.

Under one embodiment, the malodor-mitigating oral care composition comprises inulin, humectant and zinc ion source, wherein the weight ratio of inulin:humectant:zinc ion from zinc ion source is 5 to 30:20 to 40:0.5 to 10. Under one embodiment, the malodor-mitigating oral care composition comprises inulin, humectant and zinc ion source, wherein the weight ratio of inulin:humectant:zinc ion from zinc ion source is 20 to 40:10 to 30:1 to 10. Under one embodiment, the malodor-mitigating oral care composition comprises inulin, humectant and zinc ion source, wherein the weight ratio of inulin:humectant:zinc ion from zinc ion source is 20 to 30:20 to 40:1 to 10.

Under one embodiment, the malodor-mitigating oral care composition comprises inulin, humectant and zinc ion source, wherein the weight ratio of inulin:humectant:zinc ion from zinc ion source is 5 to 20:20 to 40:0.5 to 10. Under one embodiment, the malodor-mitigating oral care composition comprises inulin, humectant and zinc ion source, wherein the weight ratio of inulin:humectant:zinc ion from zinc ion source is 20 to 40:10 to 20:1 to 10. Under one embodiment, the malodor-mitigating oral care composition comprises inulin, humectant and zinc ion source, wherein the weight ratio of inulin:humectant:zinc ion from zinc ion source is 5 to 10:20 to 40:0.5 to 10.

Under one embodiment, the malodor-mitigating oral care composition comprises inulin, humectant and zinc ion source, wherein the weight ratio of inulin:humectant:zinc ion from zinc ion source is 5 to 50:20 to 30:0.5 to 10. Under one embodiment, the malodor-mitigating oral care composition comprises inulin, humectant and zinc ion source, wherein the weight ratio of inulin:humectant:zinc ion from zinc ion source is 20 to 30:10 to 50:1 to 10. Under one embodiment, the malodor-mitigating oral care composition comprises inulin, humectant and zinc ion source, wherein the weight ratio of inulin:humectant:zinc ion from zinc ion source is 20 to 50:20 to 30:1 to 10. Under one embodiment, the malodor-mitigating oral care composition comprises inulin, humectant and zinc ion source, wherein the weight ratio of inulin:humectant:zinc ion from zinc ion source is 30 to 50:20 to 30:1 to 10. Under one embodiment, the malodor-mitigating oral care composition comprises inulin, humectant and zinc ion source, wherein the weight ratio of inulin:humectant:zinc ion from zinc ion source is 40 to 50:20 to 30:1 to 10.

Under one embodiment, the malodor-mitigating oral care composition comprises inulin, humectant and zinc ion source, wherein the weight ratio of inulin:humectant:zinc ion from zinc ion source is 5 to 40:20 to 30:0.5 to 10. Under one embodiment, the malodor-mitigating oral care composition comprises inulin, humectant and zinc ion source, wherein the weight ratio of inulin:humectant:zinc ion from zinc ion source is 20 to 30:10 to 40:1 to 10. Under one embodiment, the malodor-mitigating oral care composition comprises inulin, humectant and zinc ion source, wherein the weight ratio of inulin:humectant:zinc ion from zinc ion source is 20 to 40:20 to 30:1 to 10. Under one embodiment, the malodor-mitigating oral care composition comprises inulin, humectant and zinc ion source, wherein the weight ratio of inulin:humectant:zinc ion from zinc ion source is 30 to 40:20 to 30:1 to 10.

Under one embodiment, the malodor-mitigating oral care composition comprises inulin, humectant and zinc ion source, wherein the weight ratio of inulin:humectant:zinc ion from zinc ion source is 5 to 30:20 to 30:0.5 to 10. Under one embodiment, the malodor-mitigating oral care composition comprises inulin, humectant and zinc ion source, wherein the weight ratio of inulin:humectant:zinc ion from zinc ion source is 20 to 30:10 to 30:1 to 10. Under one embodiment, the malodor-mitigating oral care composition comprises inulin, humectant and zinc ion source, wherein the weight ratio of inulin:humectant:zinc ion from zinc ion source is 20 to 30:20 to 30:1 to 10.

Under one embodiment, the malodor-mitigating oral care composition comprises inulin, humectant and zinc ion source, wherein the weight ratio of inulin:humectant:zinc ion from zinc ion source is 5 to 20:20 to 30:0.5 to 10. Under one embodiment, the malodor-mitigating oral care composition comprises inulin, humectant and zinc ion source, wherein the weight ratio of inulin:humectant:zinc ion from zinc ion source is 20 to 30:10 to 20:1 to 10. Under one embodiment, the malodor-mitigating oral care composition comprises inulin, humectant and zinc ion source, wherein the weight ratio of inulin:humectant:zinc ion from zinc ion source is 5 to 10:20 to 30:0.5 to 10.

Under one embodiment, the malodor-mitigating oral care composition comprises inulin, humectant and zinc ion source, wherein the weight ratio of inulin:humectant:zinc ion from zinc ion source is 5 to 50:30 to 50:0.5 to 10. Under one embodiment, the malodor-mitigating oral care composition comprises inulin, humectant and zinc ion source, wherein the weight ratio of inulin:humectant:zinc ion from zinc ion source is 30 to 50:10 to 50:1 to 10. Under one embodiment, the malodor-mitigating oral care composition comprises inulin, humectant and zinc ion source, wherein the weight ratio of inulin:humectant:zinc ion from zinc ion source is 20 to 50:30 to 50:1 to 10. Under one embodiment, the malodor-mitigating oral care composition comprises inulin, humectant and zinc ion source, wherein the weight ratio of inulin:humectant:zinc ion from zinc ion source is 30 to 50:30 to 50:1 to 10. Under one embodiment, the malodor-mitigating oral care composition comprises inulin, humectant and zinc ion source, wherein the weight ratio of inulin:humectant:zinc ion from zinc ion source is 40 to 50:30 to 50:1 to 10.

Under one embodiment, the malodor-mitigating oral care composition comprises inulin, humectant and zinc ion source, wherein the weight ratio of inulin:humectant:zinc ion from zinc ion source is 5 to 40:30 to 50:0.5 to 10. Under one embodiment, the malodor-mitigating oral care composition comprises inulin, humectant and zinc ion source, wherein the weight ratio of inulin:humectant:zinc ion from zinc ion source is 30 to 50:10 to 40:1 to 10. Under one embodiment, the malodor-mitigating oral care composition comprises inulin, humectant and zinc ion source, wherein the weight ratio of inulin:humectant:zinc ion from zinc ion source is 20 to 40:30 to 50:1 to 10. Under one embodiment, the malodor-mitigating oral care composition comprises inulin, humectant and zinc ion source, wherein the weight ratio of inulin:humectant:zinc ion from zinc ion source is 30 to 40:30 to 50:1 to 10.

Under one embodiment, the malodor-mitigating oral care composition comprises inulin, humectant and zinc ion source, wherein the weight ratio of inulin:humectant:zinc ion from zinc ion source is 5 to 30:30 to 50:0.5 to 10. Under one embodiment, the malodor-mitigating oral care composition comprises inulin, humectant and zinc ion source, wherein the weight ratio of inulin:humectant:zinc ion from zinc ion source is 30 to 50:10 to 30:1 to 10. Under one embodiment, the malodor-mitigating oral care composition comprises inulin, humectant and zinc ion source, wherein the weight ratio of inulin:humectant:zinc ion from zinc ion source is 20 to 30:30 to 50:1 to 10.

Under one embodiment, the malodor-mitigating oral care composition comprises inulin, humectant and zinc ion source, wherein the weight ratio of inulin:humectant:zinc ion from zinc ion source is 5 to 20:30 to 50:0.5 to 10. Under one embodiment, the malodor-mitigating oral care composition comprises inulin, humectant and zinc ion source, wherein the weight ratio of inulin:humectant:zinc ion from zinc ion source is 30 to 50:10 to 20:1 to 10. Under one embodiment, the malodor-mitigating oral care composition comprises inulin, humectant and zinc ion source, wherein the weight ratio of inulin:humectant:zinc ion from zinc ion source is 5 to 10:30 to 50:0.5 to 10.

Under one embodiment, the malodor-mitigating oral care composition comprises inulin, humectant and zinc ion source, wherein the weight ratio of inulin:humectant:zinc ion from zinc ion source is 5 to 50:30 to 40:0.5 to 10. Under one embodiment, the malodor-mitigating oral care composition comprises inulin, humectant and zinc ion source, wherein the weight ratio of inulin:humectant:zinc ion from zinc ion source is 30 to 40:10 to 50:1 to 10. Under one embodiment, the malodor-mitigating oral care composition comprises inulin, humectant and zinc ion source, wherein the weight ratio of inulin:humectant:zinc ion from zinc ion source is 20 to 50:30 to 40:1 to 10. Under one embodiment, the malodor-mitigating oral care composition comprises inulin, humectant and zinc ion source, wherein the weight ratio of inulin:humectant:zinc ion from zinc ion source is 30 to 50:30 to 40:1 to 10. Under one embodiment, the malodor-mitigating oral care composition comprises inulin, humectant and zinc ion source, wherein the weight ratio of inulin:humectant:zinc ion from zinc ion source is 40 to 50:30 to 40:1 to 10.

Under one embodiment, the malodor-mitigating oral care composition comprises inulin, humectant and zinc ion source, wherein the weight ratio of inulin:humectant:zinc ion from zinc ion source is 5 to 40:30 to 40:0.5 to 10. Under one embodiment, the malodor-mitigating oral care composition comprises inulin, humectant and zinc ion source, wherein the weight ratio of inulin:humectant:zinc ion from zinc ion source is 30 to 40:10 to 40:1 to 10. Under one embodiment, the malodor-mitigating oral care composition comprises inulin, humectant and zinc ion source, wherein the weight ratio of inulin:humectant:zinc ion from zinc ion source is 20 to 40:30 to 40:1 to 10. Under one embodiment, the malodor-mitigating oral care composition comprises inulin, humectant and zinc ion source, wherein the weight ratio of inulin:humectant:zinc ion from zinc ion source is 30 to 40:30 to 40:1 to 10.

Under one embodiment, the malodor-mitigating oral care composition comprises inulin, humectant and zinc ion source, wherein the weight ratio of inulin:humectant:zinc ion from zinc ion source is 5 to 30:30 to 40:0.5 to 10. Under one embodiment, the malodor-mitigating oral care composition comprises inulin, humectant and zinc ion source, wherein the weight ratio of inulin:humectant:zinc ion from zinc ion source is 30 to 40:10 to 30:1 to 10. Under one embodiment, the malodor-mitigating oral care composition comprises inulin, humectant and zinc ion source, wherein the weight ratio of inulin:humectant:zinc ion from zinc ion source is 20 to 30:30 to 40:1 to 10.

Under one embodiment, the malodor-mitigating oral care composition comprises inulin, humectant and zinc ion source, wherein the weight ratio of inulin:humectant:zinc ion from zinc ion source is 5 to 20:30 to 40:0.5 to 10. Under one embodiment, the malodor-mitigating oral care composition comprises inulin, humectant and zinc ion source, wherein the weight ratio of inulin:humectant:zinc ion from zinc ion source is 30 to 40:10 to 20:1 to 10. Under one embodiment, the malodor-mitigating oral care composition comprises inulin, humectant and zinc ion source, wherein the weight ratio of inulin:humectant:zinc ion from zinc ion source is 5 to 10:30 to 40:1 to 10.

Under one embodiment, the malodor-mitigating oral care composition comprises inulin, humectant and zinc ion source, wherein the weight ratio of inulin:humectant:zinc ion from zinc ion source is 5 to 50:40 to 50:0.5 to 10. Under one embodiment, the malodor-mitigating oral care composition comprises inulin, humectant and zinc ion source, wherein the weight ratio of inulin:humectant:zinc ion from zinc ion source is 40 to 50:10 to 50:1 to 10. Under one embodiment, the malodor-mitigating oral care composition comprises inulin, humectant and zinc ion source, wherein the weight ratio of inulin:humectant:zinc ion from zinc ion source is 20 to 50:40 to 50:1 to 10. Under one embodiment, the malodor-mitigating oral care composition comprises inulin, humectant and zinc ion source, wherein the weight ratio of inulin:humectant:zinc ion from zinc ion source is 30 to 50:40 to 50:1 to 10. Under one embodiment, the malodor-mitigating oral care composition comprises inulin, humectant and zinc ion source, wherein the weight ratio of inulin:humectant:zinc ion from zinc ion source is 40 to 50:40 to 50:1 to 10.

Under one embodiment, the malodor-mitigating oral care composition comprises inulin, humectant and zinc ion source, wherein the weight ratio of inulin:humectant:zinc ion from zinc ion source is 5 to 40:40 to 50:0.5 to 10. Under one embodiment, the malodor-mitigating oral care composition comprises inulin, humectant and zinc ion source, wherein the weight ratio of inulin:humectant:zinc ion from zinc ion source is 40 to 50:10 to 40:1 to 10. Under one embodiment, the malodor-mitigating oral care composition comprises inulin, humectant and zinc ion source, wherein the weight ratio of inulin:humectant:zinc ion from zinc ion source is 20 to 40:40 to 50:1 to 10. Under one embodiment, the malodor-mitigating oral care composition comprises inulin, humectant and zinc ion source, wherein the weight ratio of inulin:humectant:zinc ion from zinc ion source is 30 to 40:40 to 50:1 to 10.

Under one embodiment, the malodor-mitigating oral care composition comprises inulin, humectant and zinc ion source, wherein the weight ratio of inulin:humectant:zinc ion from zinc ion source is 5 to 30:40 to 50:0.5 to 10. Under one embodiment, the malodor-mitigating oral care composition comprises inulin, humectant and zinc ion source, wherein the weight ratio of inulin:humectant:zinc ion from zinc ion source is 40 to 50:10 to 30:1 to 10. Under one embodiment, the malodor-mitigating oral care composition comprises inulin, humectant and zinc ion source, wherein the weight ratio of inulin:humectant:zinc ion from zinc ion source is 20 to 30:40 to 50:1 to 10.

Under one embodiment, the malodor-mitigating oral care composition comprises inulin, humectant and zinc ion source, wherein the weight ratio of inulin:humectant:zinc ion from zinc ion source is 5 to 20:40 to 50:0.5 to 10. Under one embodiment, the malodor-mitigating oral care composition comprises inulin, humectant and zinc ion source, wherein the weight ratio of inulin:humectant:zinc ion from zinc ion source is 40 to 50:10 to 20:1 to 10. Under one embodiment, the malodor-mitigating oral care composition comprises inulin, humectant and zinc ion source, wherein the weight ratio of inulin:humectant:zinc ion from zinc ion source is 5 to 10:40 to 50:1 to 10.

The present invention is also directed to an oral care product comprising the oral care composition. The oral care product means the final form which is sold or administered to the patient. The oral care product is a product that comprises mixture of chemical compounds or of chemical compositions that are applied to the oral cavity to improve the health of any portion of the patient's mouth, such as the vestibule, lips, jaw, palate, teeth, gingiva, tongue, uvula, palatoglossal arches, oropharynx, gums, palatine tonsils, and like.

Under one embodiment, the oral care product is identical to the oral care composition. Under an alternative embodiment, the oral care product comprises the oral care composition and other ingredients.

The form of the oral care composition or oral care product is a liquid, a fluid, a gel, or a paste.

Examples of oral care products include toothpaste, oral rinse, mouthrinse, denture cleaner, and saliva substitute.

Mouthwash, mouth rinse, or oral rinse is a liquid which is held in the mouth passively or swilled around the mouth of a patient by contraction of the perioral muscles and/or movement of the head of the patient, and may be gargled, where the head is tilted back and the liquid bubbled at the back of the mouth. Under one embodiment, mouthwashes are antiseptic solutions intended to reduce the microbial load in the oral cavity. A mouthwash may be given for other reasons, such as for their analgesic, anti-inflammatory or anti-fungal action. Additionally, some rinses act as saliva substitutes to neutralize acid and keep the mouth moist in xerostomia. Cosmetic mouthrinses temporarily control or reduce bad breath and leave the mouth with a pleasant taste.

Toothpaste is a paste or gel dentifrice used with a toothbrush to clean and maintain the aesthetics and health of teeth. Toothpaste is used to promote oral hygiene: it is an abrasive that aids in removing dental plaque and food from the teeth, assists in suppressing halitosis, and delivers active ingredients to help prevent tooth decay and gum disease.

The present invention is also directed to a toothpaste comprising the oral care composition. The oral care product comprises toothpaste ingredients usually found in toothpastes. Examples of such ingredients include a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a fluoride source, a viscosity modifier, and a mixture thereof.

The compositions may contain anionic, cationic, nonionic and/or zwitterionic detergents or surfactants. Examples include: (a) water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, (b) higher alkyl sulfates, such as sodium lauryl sulfate, iii. higher alkyl-ether sulfates, e.g., of formula $CH_3(CH_2)_mCH_2(OCH_2CH_2)_nOSO_3X$, wherein m is 6 to 16, e.g., 10, n is 1 to 6, e.g., 2, 3 or 4, and X is Na or K, for example sodium laureth-2 sulfate ($CH_3(CH_2)_{10}CH_2(OCH_2CH_2)_2OSO_3Na$; (c) higher alkyl aryl sulfonates such as sodium dodecyl benzene sulfonate (sodium lauryl benzene sulfonate); (d) higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at 0.3% to 4.5% by weight, e.g., 1.5%. The compositions may optionally contain mixtures of surfactants, e.g., comprising anionic surfactants and other surfactants that may be anionic, cationic, zwitterionic or nonionic. Generally, surfactants are those which are reasonably stable throughout a wide pH range. In certain embodiments, the anionic surfactants useful herein include the water-soluble salts of alkyl sulfates having 10 to 18 carbon atoms in the alkyl radical and the water-soluble salts of sulfonated monoglycerides of fatty acids having 10 to 18 carbon atoms. Sodium lauryl sulfate, sodium lauroyl sarcosinate and sodium coconut monoglyceride sulfonates are examples of anionic surfactants of this type. In a particular embodiment, the composition comprises sodium lauryl sulfate. The surfactant or mixtures of compatible surfactants can be present in the composition in 0.1% to 5%, in another embodiment 0.3% to 3% and in another embodiment 0.5% to 2% by weight of the total composition.

In some embodiments, the oral care composition comprises a desensitizing agent. Suitable desensitizing agents include, without limitation, potassium tartrate, potassium bicarbonate, potassium oxalate, potassium nitrate, strontium salts and mixtures thereof.

In some embodiments, the oral care composition includes a tartar control (anticalculus) agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers.

In some embodiments, the oral care composition contains a binder agent; any conventional binder agent may be utilized. Suitable agents include marine colloids, carboxyvinyl polymers, carrageenans, starches, cellulosic polymers such as hydroxyethylcellulose, carboxymethylcellulose (carmellose), hydroxypropyl methyl cellulose and salts thereof (e.g., carmellose sodium), natural gums such as karaya, xanthan, gum arabic and tragacanth, chitosan, colloidal magnesium aluminum silicate, and colloidal silica.

In some embodiments, the oral care composition includes a thickening agent. The thickening agent, such as crosslinked polyvinvlpyrrolidone and/or fumed silica, is provided which thickens the composition to enable the composition to be extruded by a patient or user from a container such as a tube to enable the composition to be used as a toothpaste or gel, and to be readily manufactured, in particular so as to be pumpable. In some embodiments, the crosslinked polyvinvlpyrrolidone and/or fumed silica thickening agent is present in an amount of from 1 wt % to 5 wt %, based on the weight of the composition.

Further, the oral care composition may optionally comprise an additional orally acceptable thickening agent, selected from one or more of, without limitation, carbomers, also known as carboxyvinyl polymers, carrageenans, also known as Irish moss and more particularly carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, and colloidal magnesium aluminum silicate and mixtures of the same. Optionally, such additional thickening agents are present in a total amount of about 0.1 wt % to about 50 wt %, for example about 0.1 wt % to about 35 wt % or about 1 wt % to about 15 wt %, based on the weight of the composition.

In some embodiments, the oral care composition comprises an adhesion agent. As referred to herein, an adhesion agent is a material or combination of materials that enhance the retention of the peroxide complex on the oral cavity surface onto which the composition is applied. Such adhesion agents include adhesives, film forming materials, viscosity enhancers and combinations thereof. Such materials include hydrophilic organic polymers, hydrophobic organic polymers, silicone gums, silicas, and combinations thereof. Adhesion agents are preferably present at a level of from about 0.01% to about 75%, optionally from about 1% to about 40%.

In some embodiments, the oral care composition of the invention comprises at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

In some embodiments, the oral care composition of the invention comprises at least one mouth-feel agent. Mouth-feel agents that may be incorporated into the compositions defined herein include materials which impart a desirable texture or other feeling during use of the floss. Such agents include bicarbonate salts, which may impart a "clean feel" to teeth. Any orally acceptable bicarbonate can be used, including, without limitation, alkali metal bicarbonates such as sodium and potassium bicarbonates, ammonium bicarbonate, and mixtures thereof.

In some embodiments, the oral care composition of the invention comprises at least one sweetener. Sweeteners which may be used in the compositions of the present invention include artificial sweeteners such as saccharin, acesulfam, neotam, cyclamate or sucralose; natural high-intensity sweeteners such as thaumatin, stevioside or glycyrrhizin; or sugar alcohols such as sorbitol, xylitol, maltitol or mannitol.

In some embodiments, the oral care composition of the present invention, comprises one or more flavorants. Any suitable flavorant, e.g., sweetening agent, may be employed including, without limitation, flavoring oils (e.g., oil of spearmint, peppermint, wintergreen, clove, sage, eucalyptus, marjoram, cinnamon, lemon, and orange), sucrose, sucralose, lactose, maltose, xylitol, stevia, sodium cyclamate, perillartine, aspartame, liquorice, saccharin or a salt thereof, and a combination of two or more thereof. In some embodiments, the flavorant is sodium saccharin. In some embodiments, the oral care composition comprises the one or more flavorants in an amount of about 0.1 to about 5 wt %.

In some embodiments, the oral care composition of the present invention, comprises one or more coloring agent or colorants. Such colorants may be selected from pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, magnesium silicate, silica, titanium dioxide, zinc oxide, red, yellow, brown and black iron oxides, ferric ammonium ferrocyanide, manganese violet, ultramarine, titanated mica, bismuth oxychloride, and mixtures thereof. One or more colorants are optionally present in a total amount of about 0.001 wt % to about 20 wt %, for example about 0.01 wt % to about 10 wt % or about 0.1 wt % to about 5 wt %.

In some embodiments, the oral care composition of the present invention comprises a source of fluoride ions or a fluorine-providing ingredient in amounts sufficient to supply 25 ppm to 5,000 ppm of fluoride ions, generally at least 500 ppm, e.g., 500 to 2000 ppm, e.g., 1000 to 1600 ppm, e.g., 1450 ppm. Fluoride ion sources may be added to the compositions of the invention at a level of 0.01 weight % to 10 weight %, 0.03 weight % to 5 weight %, preferably 0.1 weight % to 1 weight %, most preferably 0.5 to 0.9 weight % of the composition. However, it is to be understood that the weights of fluoride salts to provide the appropriate level of fluoride ion will obviously vary based on the weight of the counter ion in the salt, and one of skill in the art may readily determine such amounts. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source preferably includes stannous fluoride, sodium fluoride, amine fluorides, sodium monofluorophosphate, as well as mixtures thereof.

In some embodiments, the present invention provides an oral care composition comprising: a fructan; a xylitol; and a zinc ion source.

Fructans or fructosans are oligosaccharides or polysaccharides comprising a sequence of anhydrofructose units optionally combined with one or more different saccharide residues of the fructose. Fructans can be linear or branched. Fructans can be products obtained directly from a plant or microbial source or else products with a chain length which has been modified (increased or reduced) by splitting, synthesis or hydrolysis, in particular of the enzymatic variety. Fructans generally have a degree of polymerization from 2 to approximately 1 000 and preferably from 3 to approximately 60.

Three groups of fructans are distinguished. The first group corresponds to products with fructose units which are mostly bonded via β-2-1 bonds. These are essentially linear fructans, such as inulins. The second group also corresponds to linear fructoses but the fructose units are essentially bonded via β-2-6 bonds. These products are levans. The third group corresponds to mixed fructans, that is to say fructans having β-2-6 and β-2-1 sequences. These are essentially branched fructans, such as graminans.

In some embodiments, the fructan is an inulin. Inulin can be obtained, for example, from chicory, the dahlia or Jerusalem artichokes.

In some embodiments, the fructan is used in an amount of between 0.01 and 10% by weight with respect to the total weight of the composition. In other embodiments, the fructan is used in an amount between 0.1 and 7.5% by weight with respect to the total weight of the composition and more preferably still between 0.5 and 5% by weight.

The oral care composition of the present invention is designed to mitigate oral malodor. The term "mitigating" or "mitigation" and like, refer to any decrease or elimination of malodor.

As used herein, oral malodor, also called oral malodor, halitosis or bad breath, is universally experienced condition that has a variety of etiologic factors. It is extremely common and majority of adult population have had it at some point in time. Under one embpdment, oral malodor refers to the odor originated by gram-negative, anaerobic bacteria. Under one embodiment, oral malodor refers to the unpleasant smell of breath mainly originated from volatile sulfide compounds (VSCs), including hydrogen sulfide ($H_2S$), methylmercaptan ($CH_3SH$), and dimethylsulfide [$(CH_3)_2S$] resulting from the proteolytic degradation of peptides present in saliva, shed epithelium, food debris and gingival crevicular fluid.

The present invention is also directed to a method of mitigating oral malodor of a patient's oral cavity by applying the oral care product to a portion of the patient's oral cavity.

The application of the patient's oral cavity may be performed in any manner that delivers the oral care composition to at least a part of the patient's mouth. The phrase "a part of the patient's mouth" includes parts such as the vestibule, lips, jaw, palate, teeth, gingiva, tongue, uvula, palatoglossal arches, oropharynx, gums, palatine tonsils, and like.

The oral care product in form of a toothpaste comprising oral care composition, may be performed as recommended by dentists and other oral health care professionals. Proper brushing takes at least two minutes. To properly brush the patient's teeth, short, gentle strokes may be used, paying extra attention to the gumline, hard-to-reach back teeth and areas around fillings, crowns or other restoration. The brushing concentrates on thoroughly cleaning each section as follows: (a) cleaning the buccal and labial surfaces of the upper teeth, then the lower teeth; (b) cleaning the lingual surfaces of the upper teeth, then the lower teeth; (c) clean the occlusal and incisal surfaces; and (d) brushing the tongue.

The oral care product in the form of an ingestible or non-ingestible solid, powder, or liquid; or a mouthwash, comprising any one of the oral care compositions described herein, may be performed as recommended by dentists and other oral health care professionals. Examples of application of mouthwash may include the following steps: (a) pouring 20 mL of the mouthwash into a cup; (b) emptying the contents of the cup into the patient's mouth; (c) swishing the mouthwash within the oral cavity for about 30 seconds; (d) gargling in the mouth; and (e) spit the mouthwash out in the sink.

EXAMPLES

Example 1

A dose-response study was designed to determine the effect of inulin on oral microbiota in humans as a prebiotic. One of the purposes of this experiment was to determine the selective growth of health-associated oral bacteria due to inulin fermentation. Another purpose of this experiment was to identify formulation dosage levels.

Monocultures of oral health-associated bacteria (*S. salivarius, S. oralis, S. sanguinis*) and malodor-associated bacteria (*F. nucleatum, V. parvula*) were incubated in 0, 0.5, 1, 2, 3, 4, and 5% inulin.

The growth of the bacteria was quantified using optical density at $\lambda=610$ nm ("OD610") on six samples. Statistical significance of optical density differences was determined using one-way ANOVA test at 95% confidence level with a Tukey pairwise comparison test. The optical density data is shown in Table 1 (below).

TABLE 1

| % | Oral health-associated bacteria | | | Oral malodor-associated bacteria | |
|---|---|---|---|---|---|
| Inulin | S oralis | S salivarius | S sanguinis | F nucleatum | V parvula |
| 0 | 0.056 | 0.086 | 0.096 | 0.267 | 0.071 |
| 0.5 | 0.109 | 0.432 | 0.230 | 0.278 | 0.074 |
| 1.0 | 0.184 | 0.345 | 0.259 | 0.295 | 0.073 |
| 2.0 | 0.210 | 0.225 | 0.241 | 0.319 | 0.075 |
| 3.0 | 0.197 | 0.196 | 0.217 | 0.326 | 0.074 |
| 4.0 | 0.203 | 0.273 | 0.193 | 0.323 | 0.072 |
| 5.0 | 0.184 | 0.260 | 0.198 | 0.299 | 0.071 |

Further, the growth of the bacteria was also quantified by observing the decrease in pH relative to baseline. The data for the pH unit decrease is shown in Table 2 (below).

TABLE 2

| % | Oral health-associated bacteria | | | Oral malodor-associated bacteria | |
|---|---|---|---|---|---|
| Inulin | S oralis | S salivarius | S sanguinis | F nucleatum | V parvula |
| 0 | 0.617 | 1.279 | 2.009 | 0.799 | −0.378 |
| 0.5 | 1.160 | 2.800 | 2.470 | 0.918 | −0.376 |
| 1 | 2.020 | 2.853 | 2.436 | 1.008 | −0.366 |
| 2 | 2.444 | 2.858 | 2.341 | 1.162 | −0.361 |
| 3 | 2.444 | 2.698 | 2.203 | 1.164 | −0.283 |
| 4 | 2.387 | 2.544 | 2.068 | 1.163 | −0.315 |
| 5 | 2.232 | 2.416 | 1.947 | 1.059 | −0.264 |

An increase of the optical density is indicative of bacterial growth. Table 1 shows that the optical density of the tested oral health-associated bacteria (*S. oralis*, *S. salivarius*, and *S. sanguinis*) significantly increased in the presence of inulin at all tested concentrations relative to untreated (0% inulin), indicating inulin fermentation.

Further, for two of the three oral health-associated bacteria (with *S. salivarius* being the exception), decrease in pH correlated with growth for all tested concentrations.

Still further, Table 1 shows that the optical density of the tested oral malodor-associated bacteria (*F. nucleatum*, *V. parvula*) in the presence of inulin was parity to untreated (0% inulin) at all tested concentrations, indicating lack of inulin fermentation.

Example 2

An in vitro malodor study was conducted to evaluate the effect of various combinations of inulin and xylitol with zinc on oral malodor. Malodor is a combination of hydrogen sulfide and other volatile compounds. Microbial growth as measured by OD610, and fermentation, as measured by pH (confounding variables that impact oral malodor) were also evaluated.

Whole human saliva was collected from four donors, pooled and suspended in growth medium at a 2% final concentration. Stock, simple solutions of inulin, xylitol, and zinc citrate were prepared in growth medium and incorporated according to the experiment design specified in Table 3 (below). Treatment suspensions were incubated overnight in sterilized headspace vials.

TABLE 3

| Example | Description |
|---|---|
| 1 | medium only (i.e. no salivary inoculum) |
| 2 | Untreated |
| 3 | 0.2% inulin |
| 4 | 0.2% xylitol |
| 5 | 0.04% zinc citrate |
| 6 | 0.2% inulin + 0.2% xylitol |
| 7 | 0.2% xylitol + 0.04% zinc citrate |
| 8 | 0.2% inulin + 0.04% zinc citrate |
| 9 | 0.2% inulin + 0.2% xylitol + 0.04% zinc citrate |

Malodor (i.e., hydrogen sulfide and other volatile compounds) in the culture vial headspace was quantified using validated procedures on Voice200ultra SIFT-MS (Syft Technologies, Christchurch, New Zealand). Following SIFT-MS analysis, microbial growth was quantified using optical density at $\lambda=610$ nm. The data is presented in Table 4 (below).

In each of the tables below, the column labeled "Grouping" lists letter; means that do not share a grouping letter are significantly different ($p<0.05$).

TABLE 4

Microbial growth as observed by OD610

| Example | n | Mean | StDev | Grouping | | | |
|---|---|---|---|---|---|---|---|
| 1 | 6 | 0.1045 | 0.0037 | | | | D |
| 2 | 6 | 0.4317 | 0.0110 | A | B | | |
| 3 | 6 | 0.4552 | 0.0067 | A | | | |
| 4 | 6 | 0.4182 | 0.0060 | | B | | |
| 5 | 6 | 0.1407 | 0.0198 | | | C | |
| 6 | 6 | 0.4285 | 0.0126 | | B | | |
| 7 | 6 | 0.1307 | 0.0174 | | | C | D |
| 8 | 6 | 0.1295 | 0.0115 | | | C | D |
| 9 | 6 | 0.1410 | 0.0235 | | | C | |

The pH was measured using a standard pH meter by following validated procedures. Statistical significance of differences for all parameters was determined using one-way ANOVA test at 95% confidence level with a Tukey pairwise comparison test. Microbial growth and pH were used to stratify the treatments for hydrogen sulfide statistical analysis. The data is presented in Table 5 (below).

TABLE 5

| Example | n | Mean | StDev | Grouping | | | |
|---|---|---|---|---|---|---|---|
| 1 | 6 | 6.6112 | 0.0064 | A | | | |
| 2 | 6 | 5.8735 | 0.0029 | | B | | |
| 3 | 6 | 4.4977 | 0.0076 | | | | D |
| 4 | 6 | 5.9067 | 0.0052 | | B | | |
| 5 | 6 | 6.5948 | 0.0263 | A | | | |
| 6 | 6 | 4.6878 | 0.0355 | | | C | |
| 7 | 6 | 6.5957 | 0.0191 | A | | | |
| 8 | 6 | 6.5860 | 0.0228 | A | | | |
| 9 | 6 | 6.6052 | 0.0305 | A | | | |

Hydrogen sulfide in headspace of salivary inoculum was quantified using SIFT-MS validated procedure. Treatment groups were stratified based on microbial growth and pH; and are presented in Tables 6 and 7 (below).

TABLE 6

| Example | n | Mean (ppb) | StDev | Grouping | |
|---|---|---|---|---|---|
| 1 | 6 | 9.612 | 2.047 | | B |
| 5 | 6 | 21.86 | 3.12 | A | |
| 7 | 6 | 12.84 | 2.99 | | B |
| 8 | 6 | 11.797 | 2.125 | | B |
| 9 | 6 | 11.038 | 1.842 | | B |

TABLE 7

| Example | n | Mean (ppb) | StDev | Grouping | |
|---|---|---|---|---|---|
| 2 | 6 | 3212 | 1452 | A | |
| 3 | 6 | 23.75 | 11.5 | | B |
| 4 | 6 | 2243 | 2714 | A | B |
| 6 | 6 | 23.5 | 17.83 | | B |

The data in Tables 4 to 7 (above) show that all treatments containing zinc resulted in significantly lower microbial growth and significantly lower fermentation (i.e., higher pH) relative to other study treatments, with the exception of the medium negative control. With the study treatments stratified based on microbial growth and pH, in vitro treatment of whole human saliva with zinc citrate in combination with inulin, xylitol, or both inulin and xylitol, resulted in significantly lower hydrogen sulfide production (i.e., oral malodor) relative to zinc citrate alone.

While the present invention has been described with reference to several embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention is to be determined from the claims appended hereto. Further, it will be apparent to those of skill in the art that numerous changes may be made in such details without departing from the spirit and the principles of the invention.

What is claimed is:

1. An oral care composition comprising:
an effective amount of inulin, wherein the inulin is an amount from about 1 wt. % to about 3 wt. %;
a humectant, wherein the humectant comprises glycerin;
a zinc ion source, wherein the zinc ion source comprises zinc citrate;
and an orally acceptable carrier,
wherein the amount of inulin is further effective to increase the bacterial growth of S. salivarius, S. oxalis, and S. sanguinis in monocultures relative to samples that do not receive any inulin, wherein the bacterial growth is measured by optical density; and wherein all weight percentages are based on the total weight of the oral care composition.

2. The oral care composition according to claim 1, further comprising an ingredient selected from: a surfactant, a desensitizing agent, a hydrophilic polymer, a tartar control agent, a binder, a thickening agent, an adhesion agent, a foam modulator, a pH modifying agent, a mouth feel agent, a sweetener, a flavorant, a coloring agent, a fluoride source, a viscosity modifier; and a combination of two or more thereof.

3. The oral care composition according to claim 1 in a form selected from: a toothpaste; a mouthwash or mouthrinse; an ingestible or non-ingestible solid, powder, or liquid; a spray; a film; a gel; a dental powder; a prophy; and a lozenge.

4. An oral care composition comprising:
from 0.01 wt. % to about 5 wt. % of a fructan, wherein the fructan comprises an inulin;
from about 0.1 to about 5 wt. % of xylitol;
a zinc ion source that is zinc citrate; and
an orally acceptable carrier, wherein all weight percentages are based on the total weight of the oral care composition;
wherein the amount of inulin is further effective to increase the bacterial growth of S. salivarius, S. oxalis, and S. sanguinis in monocultures relative to samples that do not receive any inulin, wherein the bacterial growth is measured by optical density; and wherein all weight percentages are based on the total weight of the oral care composition.

5. A method of treating, preventing, or ameliorating a symptom associated with, a disease, disorder or condition of the oral cavity comprising applying an oral care composition according to claim 1 to a mammal in need thereof.

6. The method according to claim 5, wherein the disease, disorder or condition of the oral cavity is selected from: gingivitis; caries; oral malodor; inflammation; and periodontitis.

7. The oral care composition according to claim 4, wherein the oral care composition comprises from about 0.1 to about 5 wt. % of xylitol, and the oral care composition has a weight ratio of inulin:xylitol:zinc citrate that is from about 5:5:1.

* * * * *